US010584345B2

(12) United States Patent
Calabotta et al.

(10) Patent No.: US 10,584,345 B2
(45) Date of Patent: *Mar. 10, 2020

(54) PREPARATION AND USE OF PLANT EMBRYO EXPLANTS FOR TRANSFORMATION

(71) Applicant: MONSANTO TECHNOLOGY LLC, St. Louis, MO (US)

(72) Inventors: Beth Jo Calabotta, University City, MO (US); Kevin Lee Deppermann, Saint Charles, MO (US); Erik D. Dersch, Fitchburg, WI (US); Jerald D. Heise, St. Louis, MO (US); Angela Ranae Koestel, St. Louis, MO (US); Cindy L. Ludwig, St. Louis, MO (US); Brian J. Martinell, Mt. Horeb, WI (US); Edward Williams, Madison, WI (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/706,427

(22) Filed: Sep. 15, 2017

(65) Prior Publication Data
US 2018/0135063 A1 May 17, 2018

Related U.S. Application Data

(63) Continuation of application No. 14/642,671, filed on Mar. 9, 2015, now Pat. No. 9,790,512, which is a continuation of application No. 13/750,977, filed on Jan. 25, 2013, now Pat. No. 9,006,513, which is a continuation of application No. 12/045,498, filed on Mar. 10, 2008, now Pat. No. 8,362,317.

(60) Provisional application No. 60/894,096, filed on Mar. 9, 2007, provisional application No. 60/915,066, filed on Apr. 30, 2007.

(51) Int. Cl.
*C12N 15/82* (2006.01)
*A01H 4/00* (2006.01)
*C12N 5/04* (2006.01)
*G01N 33/00* (2006.01)
*C12N 9/10* (2006.01)

(52) U.S. Cl.
CPC ......... *C12N 15/8201* (2013.01); *A01H 4/003* (2013.01); *A01H 4/008* (2013.01); *C12N 5/04* (2013.01); *C12N 9/1029* (2013.01); *C12N 15/8202* (2013.01); *C12N 15/8205* (2013.01); *C12N 15/8209* (2013.01); *C12N 15/8271* (2013.01); *C12N 15/8274* (2013.01); *C12N 15/8275* (2013.01); *C12N 15/8277* (2013.01); *C12N 15/8281* (2013.01); *G01N 33/0098* (2013.01); *C12Y 203/01081* (2013.01)

(58) Field of Classification Search
CPC ............ C12N 15/8201; C12N 15/8202; C12N 15/8274; C12N 9/1029; C12N 15/8281; C12N 15/8205; C12N 15/8275; C12N 15/8271; C12N 5/04; C12N 15/8209; A01H 4/008; A01H 4/003; G01N 33/0098; C12Y 203/01081
USPC ........................................................ 800/278
See application file for complete search history.

(56) References Cited

U.S. PATENT DOCUMENTS

| | | | |
|---|---|---|---|
| 1,849,786 A | 3/1932 | Bloede et al. | |
| 2,283,449 A | 5/1942 | Meneux et al. | |
| 3,104,692 A | 9/1963 | Turner | |
| 3,301,292 A | 1/1967 | O'Connor | |
| 3,667,523 A | 6/1972 | Lynn et al. | |
| 3,744,399 A | 7/1973 | Bonteil | |
| 4,066,012 A | 1/1978 | Satake et al. | |
| 4,220,287 A | 9/1980 | Boczewski | |
| 4,245,553 A | 1/1981 | Nakamura | |
| 4,301,183 A | 11/1981 | Giguere | |
| 4,326,358 A * | 4/1982 | Lawrence et al. | 800/268 |
| 4,530,278 A | 7/1985 | Sarig et al. | |
| 4,986,997 A | 1/1991 | Posner et al. | |
| 5,004,863 A | 4/1991 | Umbeck | |
| 5,015,580 A | 5/1991 | Christou et al. | |
| 5,073,675 A | 12/1991 | Jones et al. | |
| 5,164,310 A | 11/1992 | Smith et al. | |
| 5,217,902 A | 6/1993 | Jones et al. | |
| 5,238,835 A | 8/1993 | McKersie et al. | |
| 5,250,313 A | 10/1993 | Giguere | |
| 5,262,316 A | 11/1993 | Engler et al. | |

(Continued)

FOREIGN PATENT DOCUMENTS

BR 9917361 5/2011
CN 1302900 A 7/2001

(Continued)

OTHER PUBLICATIONS

Use of fungicides in plant Tissue Culture Shields et al. Plant Cell Reports (1984) 3:33-36.*
Effect in Vitro Storage at 4c on survival and prolifiration of two applle root stock. Orlikowska Plant Cell Tissue and Organ Culture 31: 1-7 1992.*
Plant Cryopreservation progres and prospects Engelmann . In vitro Cell Dev. Bid. Plant 40:427-433 2004.*
U.S. Appl. No. 15/452,519, filed Mar. 7, 2017, Adams et al.
Abdelnour-Esquivel et al., "Cryopreservation of zygotic embryos of *Coffea* spp", Cryo Letters 13(5):297-302, 1992.

(Continued)

*Primary Examiner* — Annette H Para
(74) *Attorney, Agent, or Firm* — Dentons US LLP; David Lanzotti, Esq.

(57) ABSTRACT

The present invention relates to excision of explant material comprising meristematic tissue from seeds, and storage of such material prior to subsequent use in plant tissue culture and genetic transformation. Methods for tissue preparation, storage, and transformation are disclosed, as is transformable meristem tissue produced by such methods, and apparati for tissue preparation.

21 Claims, 11 Drawing Sheets

(56) References Cited

U.S. PATENT DOCUMENTS

| | | | |
|---|---|---|---|
| 5,286,635 A | 2/1994 | Hanson et al. | |
| 5,368,778 A | 11/1994 | Shimotomai et al. | |
| 5,379,952 A | 1/1995 | Geiger | |
| 5,415,085 A | 5/1995 | Thomson | |
| 5,538,880 A | 7/1996 | Lundquist et al. | |
| 5,550,318 A | 8/1996 | Adams et al. | |
| 5,563,055 A | 10/1996 | Townsend et al. | |
| 5,567,599 A | 10/1996 | Lemieux | |
| 5,591,616 A | 1/1997 | Hiei et al. | |
| 5,678,477 A | 10/1997 | Satake et al. | |
| 5,693,512 A | 12/1997 | Finer et al. | |
| 5,731,179 A | 3/1998 | Komari et al. | |
| 5,767,366 A | 6/1998 | Sathasivan et al. | |
| 5,824,877 A | 10/1998 | Hinchee et al. | |
| 5,846,797 A * | 12/1998 | Strickland | 800/294 |
| 5,914,451 A * | 6/1999 | Martinell et al. | 800/300 |
| 5,952,230 A | 9/1999 | Kim et al. | |
| 5,981,840 A | 11/1999 | Zhao et al. | |
| 6,070,815 A | 6/2000 | Miyatake | |
| 6,140,555 A | 10/2000 | Reichert et al. | |
| 6,153,813 A | 11/2000 | Reichert et al. | |
| 6,265,638 B1 | 7/2001 | Bidney | |
| 6,307,127 B1 | 10/2001 | Jorsboe et al. | |
| 6,384,301 B1 * | 5/2002 | Martinell et al. | 800/294 |
| 6,422,137 B1 | 7/2002 | Nakhei-Nejad | |
| 6,581,535 B2 | 6/2003 | Barry et al. | |
| 6,900,057 B2 | 5/2005 | Burns et al. | |
| 6,936,294 B2 | 8/2005 | Matthews et al. | |
| 7,002,058 B2 | 2/2006 | Martinell et al. | |
| 7,057,089 B2 | 6/2006 | Ranch et al. | |
| 7,067,834 B2 | 6/2006 | Horigane et al. | |
| 7,150,993 B2 | 12/2006 | Davis et al. | |
| 7,154,027 B2 | 12/2006 | Demmer et al. | |
| 7,229,034 B2 | 6/2007 | Feazel et al. | |
| 7,279,336 B2 | 10/2007 | Gelvin et al. | |
| 7,288,694 B2 | 10/2007 | Armstrong et al. | |
| 7,345,218 B1 | 3/2008 | Jiao et al. | |
| 7,402,734 B2 | 7/2008 | Martinell et al. | |
| 7,524,522 B2 | 4/2009 | DeLine et al. | |
| 7,560,611 B2 | 7/2009 | Adams et al. | |
| 7,658,033 B2 | 2/2010 | Martinell et al. | |
| 7,694,457 B2 | 4/2010 | Martinell et al. | |
| 7,888,552 B2 | 2/2011 | Ye et al. | |
| 7,935,529 B2 | 5/2011 | Davis et al. | |
| 7,937,890 B2 | 5/2011 | Adams et al. | |
| 7,938,345 B2 | 5/2011 | Teeter, Jr. et al. | |
| 8,030,544 B2 | 10/2011 | Martinell et al. | |
| 8,044,260 B2 | 10/2011 | Dersch et al. | |
| 8,323,974 B2 | 12/2012 | Davis et al. | |
| 8,362,317 B2 | 1/2013 | Calabotta et al. | |
| 8,609,934 B2 | 12/2013 | Fillatti et al. | |
| 8,937,216 B2 | 1/2015 | Dersch et al. | |
| 2002/0120961 A1 | 8/2002 | Ranch et al. | |
| 2002/0184663 A1 | 12/2002 | Sun et al. | |
| 2002/0192040 A1 | 12/2002 | McKinnis | |
| 2003/0018995 A1 | 1/2003 | Dresselhous et al. | |
| 2003/0074686 A1 | 4/2003 | Heinz et al. | |
| 2004/0034889 A1 | 2/2004 | Khan | |
| 2004/0043117 A1 | 3/2004 | Cope et al. | |
| 2005/0005321 A1 * | 1/2005 | Martinell et al. | 800/278 |
| 2005/0042305 A1 | 2/2005 | Endo et al. | |
| 2005/0044595 A1 | 2/2005 | Arias et al. | |
| 2005/0158699 A1 | 7/2005 | Kadkade et al. | |
| 2006/0005273 A1 | 1/2006 | Rudrabhatla et al. | |
| 2006/0059589 A1 | 3/2006 | Martinell et al. | |
| 2006/0260012 A1 | 11/2006 | Khan | |
| 2007/0039075 A1 | 2/2007 | Tissot et al. | |
| 2011/0271410 A1 | 11/2011 | Adams et al. | |
| 2012/0054918 A1 | 3/2012 | Dersch et al. | |
| 2015/0007370 A1 | 1/2015 | Adams et al. | |
| 2015/0121574 A1 | 4/2015 | Dersch et al. | |
| 2018/0148730 A1 | 5/2018 | Dersch et al. | |

FOREIGN PATENT DOCUMENTS

| | | |
|---|---|---|
| CN | 1838995 A | 9/2006 |
| EP | 0298722 | 1/1989 |
| EP | 0 339 577 | 11/1989 |
| EP | 0 356 987 | 3/1990 |
| EP | 0380055 | 8/1990 |
| EP | 0740897 B1 | 11/1999 |
| EP | 0958863 | 11/1999 |
| EP | 1142489 | 10/2001 |
| EP | 1 236 801 | 9/2002 |
| GB | 402848 | 12/1933 |
| GB | 439399 | 12/1935 |
| GB | 657644 | 9/1951 |
| GB | 861711 | 2/1961 |
| GB | 1459551 | 12/1976 |
| JP | 59-082063 | 5/1984 |
| JP | 10-276748 | 10/1998 |
| JP | 11-164678 | 6/1999 |
| JP | 017107 | 1/2001 |
| JP | 292717 | 10/2001 |
| JP | 2002-19886 A | 4/2002 |
| JP | 2003-339395 | 12/2003 |
| JP | 2004-357547 | 12/2004 |
| WO | WO 92/15675 | 9/1992 |
| WO | WO 95/06722 | 9/1995 |
| WO | WO 96/10341 | 4/1996 |
| WO | WO 98/01575 | 1/1998 |
| WO | WO 99/02267 | 1/1999 |
| WO | WO 99/10513 | 3/1999 |
| WO | WO 99/20776 | 4/1999 |
| WO | WO 00/42207 | 7/2000 |
| WO | WO 2000/077230 | 12/2000 |
| WO | WO 01/29241 | 4/2001 |
| WO | WO 02/00010 | 1/2002 |
| WO | WO 02/37987 | 5/2002 |
| WO | WO 02/066599 | 8/2002 |
| WO | WO 03/017752 | 3/2003 |
| WO | WO 2003/0017752 | 3/2003 |
| WO | WO 03/100381 | 12/2003 |
| WO | WO 2004/000006 | 12/2003 |
| WO | WO 2004/006667 | 1/2004 |
| WO | WO 2005/000471 | 1/2005 |
| WO | WO 2005/122750 | 12/2005 |
| WO | WO 2006/026466 | 3/2006 |
| WO | WO 2007/079538 | 7/2007 |
| WO | WO 2007/103769 | 9/2007 |

OTHER PUBLICATIONS

Aitken-Christie et al., "Automation and Environmental Control in Plant Tissue Culture", Kluwer Academic Publishers, Netherlands, 1995.

Aragao et al., "Germ line genetic transformation in cotton (*Gossypium hirsutum* L.) by selection of transgenic meristematic cells with a herbicide molecule," Plant Sci., 168:1227-1233, 2005.

Baker et al., "High frequency somatic embryogenesis in peanut using mature dry seed," Plant Cell Reports; 15:38-42; 1995.

Bechtold et al., "The maternal chromosome set is the target of the T-DNA in the in planta transformation of *Arabidopsis thaliana*," Genetics, 155:1875-1887, 2000.

Birch, R. G., "Plant Transformation: Problems and Strategies for Practical Application", Annu. Rev. Plant Physiol. Plant Mol. Biol., 48:297-326, 1997.

Bouchez et al., "A binary vector based on basta resistance for in planta transformation of *Arabidopsis thaliana*," Comptes Rendus des Seances de L'Academie des Sciences, Series II: Sciences de la Vie, 316:1188-1193, 1993.

Bretagne-Sagnard et al., "Selection of transgenic flax plants is facilitated by spectinomycin," Transgenic Res., 5:131-137, 1996.

Broothaerts et al., "Gene transfer to plants by diverse species of bacteria," Nature, 433:629-633, 2005.

Buchheim et al., "Maturation of Soybean Somatic Embryos and the Transition of Plantlet Growth" Plant Physiol., 89:768-775, 1989.

Chai et al., "Optimum moisture content of seeds stored at ambient temperatures," Seed Science Research, 8(Supp. 1):23-23, 1998.

(56) References Cited

OTHER PUBLICATIONS

Chandra et al., "Regeneration and genetic transformation of grain legumes: An overview," Current Science, 84:(3):381-387, 2003.
Chaudhary et al., "Slow desiccation leads to high-frequency shoot recovery from transformed somatic embryos of cotton (*Gossypium hirsutum* L. cv. Coker 310 FR)," Plant Cell Rep., 21:955-960, 2003.
Chen et al., "A comparison of methods for delivering DNA to wheat: the application of wheat dwarf virus DNA to seeds with exposed apical meristems," Transgenic Res., 1:93-100, 1992.
Chen et al., "Factors influencing agrobacterium-mediated transformation of monocotyledonous species," In Vitro Cell Dev. Biol., 40:31-45, 2004.
Chen, Database WPI Week 200432, Oct. 21, 2003.
Chengalrayan et al., "High-frequency conversion of abnormal peanut somatic embryos," Plant Cell Reports, 16:783-786, 1997.
Delporte et al., "Plant regeneration through callus initiation from thin mature embryo fragments of wheat," Plant Cell, Tissue and Organ Culture, 67:73-80, 2001.
English translation of office action issued in Chinese Patent Application No. 200880007599.4 dated Aug. 10, 2011.
Finer et al., "Transformation of soybean via particle bombardment of embryogenic suspension culture tissue," In Vitro Cell. Dev. Biol., 27:175-182, 1991.
Francois et al., "Different approaches for multi-transgene-stacking in plants," Plant Sci., 163:281-295, 2002.
Grandison et al., "Separation Process in the Food and Biotechnology Industries, Principles and Applications," Woodhead Publishing Limited, 266-286, 1995.
Green et al., "Plant regeneration from tissue cultures," Crop Sci., 15:417-421, 1975.
Haris et al., "Transformation of cotton (*Gossypium hirsutum* L.) with insect resistant gene by particle bombardment and agrobacterium," Pakl. J. of Biological Sci., 1:170-174, 1988.
Hewezi et al., "Dehydrating immature embryo split apices and rehydrating with agrobacterium tumefaciens: a new method for genetically transforming recalcitrant sunflower," Plant MoL Biol. Reporter, 20:335-345, 2002.
Higley et al., "Effects of non-destructive tissue extraction on the viability of corn, soybean, and bean seeds", Seed Science and Technology, 22(2):245-252, 1994.
Hinchee et al., "Production of transgenic soybean plants using agrobacterium-mediated DNA transfer," Bio/Technology, 6:915-922, 1988.
Hussain et al., "Sonication assisted agrobacterium mediated transformation (SAAT): an alternative method for cotton transformation," Pak. J. Bot., 39(1):223-230, 2007.
Ibaraki et al., "Automation of somatic embryo production," Plant Cell, Tissue and Organ Culture, 65:179-199, 2001.
Johnston et al., "Mass Isolation of Viable Wheat Embryos," Nature, 179:160-161, 1957.
Jones et al., "Effective vectors for transformation, expression of heterologous genes, and assaying transposon excision in transgenic plants," Transgenic Res., 1:285-297, 1992.
Kameswara Rao Plant Genetic resources: Advancing conservation and use through biotechnology. African J of Biotechnol; vol. 3(2) pp. 136-145; Feb. 2004.
Kern, "Comparison between Wheat Embryos Isolated Mechanically and by Floating off from Organic Solvents," Biologia Plantarum (PRAHA), 17(4):309-313, 1975.
Kingsley, "Introductory Plant Biology," The McGraw-Hill Companies Inc., Eighth Edition, 2000.
Kofer et al., "PEG-mediated plastid transformation in higher plants," In Vitro Cell Dev. Biol.—Plant, 34:303-309, 1998.
Krochko et al., Abstract Only, "Seed storage proteins in developing somatic embryos of alfalfa: defects in accumulation compared to zygotic embryos," J. Exp. Bot.; 45:699-708: 1994.
Krysan, "Ice-Cap. A high-throughput method for capturing plant tissue samples for genotype analysis," Plant Physiology, 135:1162-1169, 2004.

Kumar et al., "Sable transformation of the cotton plastid genome and maternal inheritance of transgenes," Plant Mol. Biol., 56:203-216, 2004.
Kumelehn et al., "In vitro development of wheat (*Triticum aestivum* L. from zygote to plant via ovule culture," Plant Cell Rep., 16:663-667, 1997.
Lacorte et al., "Transient expression of GUS and the 2S albumin gene from Brazil nut in peanut (*Arachis hypogaea* L.) seed explants using particle bombardment," Plant Cell Reports, 16:619-623, 1997.
Larkin et al., "Transgenic white clover. Studies with the auxin-responsive promoter, GH3, in root gravitropism and lateral root development," Transgenic Res., 5:325-335, 1996.
Laurie et al., "A novel technique for the partial isolation of maize embryo sacs and subsequent regeneration of plants," In Vitro Cell Dev. Biol.—Plant, 35:320-325, 1999.
Li et al., "Improvement of cotton fiber quality by transforming the acsA and acsB genes into *Gossypium hirsutum* L. by means of vacuum infiltration," Plant Cell Rep., 22:691-697, 2004.
Lim et al., "Construction of small binary vectors for agrobacterium-mediated transformation in plants," J. of Plant Biol., 42:317-320, 1999.
Lim et al., "Expression of the glutathione S-transferase gene (NT107) in transgenic Dianthus superbus," Plant Cell, Tissue and Organ Culture, 80:277-286, 2005.
Livingstone et al., "Efficient transformation and regeneration of diverse cultivars of peanut (*Arachis hypogaea* L.) by particle bombardment into embryogenic callus produced from mature seeds," Molecular Breeding, 5:43-51, 1999.
Lowe et al., "Germline transformation of maize following manipulation of chimeric shoot meristems," Bio/Technology, 13:677-682, 1995.
Mahalakshmi et al., "Exogenous DNA Uptake via Cellular Permeabilization and Expression of Foreign Gene in Wheat Zygotic Embryos," Plant Biotechnology, 17(3)235240, 2000.
Malone-Schoneberg et al., "Stable transformation of sunflower using Agrobacterium and split embryonic axis explants," Plant Science, 103:199-207, 1994.
Marcus et al., "The Wheat Embryo Cell-Free System," Methods of Enzymology, 30:749-754, 1974.
Matthys-Rochon, "In vitro development of maize immature embryos: a tool for embryogenesis analysis," Journal of Experimental Botany 49(322):839-845, 1998.
McCabe et al., "Stable transformation of soybean (*Glycine max*) by particle acceleration," Bio/Technology, 6:923-926, 1988.
McCabe et al., "Transformation of elite cotton cultivars via particle bombardment of meristems," Bio/Technology, 11:596-598, 1993.
McKersie et al., "Drying somatic embryos for use as artificial seeds," Proc. Plant Growth Regulation Soc. America., p. 199-207, 1990.
McKersie et al., "Application of artificial seed technology in the production of hybrid alfalfa (*Medicago sativa* L.)," In Vitro Cell Dev. Biol., 25:1183-1188, 1989.
Miki et al., "Procedures for introducing foreign DNA into plants," In: Methods in Plant Molecular Biology and Biotechnology, Glick et al. (Eds.), CRC Press, Inc., Boca Raton, FL, D.67-88. 1983.
Moon et al., "Effects of proliferation, maturation, and desiccation methods on conversion of soybean somatic embryos", In vitro Cellular & Developmental Biology—Plant 39(6):623628, 2003.
Nghi et al., "Performance of a plate mill and a modified Engelberg huller for small-scale dry milling and de-germing of maize," International Journal of Food Science and Technology, 29:347-353, 1994.
Notice of Opposition regarding European Patent No. 1,635,949, dated Oct. 5, 2011.
Oreifig et al., "Development of a non-lethal selection system by using the aadA marker gene for efficient recovery of transgenic rice (*Oryza sativa* L.)," Plant Cell Reports, 22:490-496, 2004.
Orlikowska et al., "Effect of in vitro storage at 4° C. on survival and proliferation of two apple root stock," Plant Cell, Tissue and Organ Culture, 31:1-7, 1992.
Patnaik et al., "Agrobacterium-mediated transformation of mature embryos of triticum aestivum and triticum durum," Current Sci., 91(3):307-317, 2006.

(56) References Cited

OTHER PUBLICATIONS

Paz et al., "Improved cotyledonary node method using an alternative explant derived from mature seed for efficient agrobacterium-mediated soybean transformation," Plant Cell Rep., 25:206-213, 2006.
PCT Search Report for Application No. PCT/US2008/056411 dated Oct. 2, 2008.
Pollard et al., "Plant and Cell Tissue Culture," Methods in Molecular Biology, vol. 6, 1990.
Popelka et al., "Genetic transformation of cowpea (*Vigna unguiculata* L.) and stable transmission of the transgenes to progeny," Plant Cell Rep., 25:304-312, 2006.
Rohini et al., "Transformation of peanut (*Arachis hypogaea* L.): a non-tissue culture based approach for generating transgenic plants," Plant Sci., 150:41-49, 2000.
Sandvang, "Novel streptomycin and spectinomycin resistance gene as a gene cassette within a class 1 integron isolated from *Escherichia coli*," Antimicrobial Agents and Chemotherapy, 43(12):3036-3038, 1999.
Sawahel et al., "Stable Genetic Transformation of Mature Wheat Embryos using Silicone Carbide Fibers and DNA Imbibition," Cellular and Molecular Biology Letters, 2:421-429, 1997.
Schnall et al., "Culturing peanut (*Arachis hypogaea* L.) zygotic embryos for transformation via microprojectile bombardment," Plant Cell Reports, 12:316-319, 1993.
Schnug et al., "Preparation techniques of small sample sizes for sulphur and indirect total glucosinolate analysis in brassica seeds by X-ray fluorescence spectroscopy," Fett Sci. Tech., 9:334-337, 1993.
Schroder et al., "Transformation of *Brassica napus* by using the aadA gene as selectable marker and inheritance studies of the marker genes," Physiologia Plantarum, 92:37-46, 1994.
Senaratna et al., "Artificial seeds of alfalfa (*Medicago sativa* L.) induction of desiccation tolerance in somatic embryos," In Vitro Cell. Dev. Biol., 26:85-90, 1990.
Senaratna et al., "Dehydration injury in germinating soybean (*Glycine max* L. merr.) seeds," Plant Physiology, 72:620-624, 1983.
Senaratna et al., "Desiccation tolerance of alfalfa (*Medicago sativa* L.) somatic embryos. Influence of abscisic acid, stress pretreatments and drying rates," Plant Sci., 35:253-259, 1989.
Senaratna et al., "Direct DNA uptake during the imbibition of dry cells," Plant Sci., 79:223-228, 1991.
Shields et al., "Use of fungicides in plant tissue culture," Plant Cell Reports, 3:33-36, 1984.
Simoens et al., "A binary vector for transferring genomic libraries to plants," Nucleic Acids Research, 14:8073-8090, 1988.
Statement from Dr. William J. Gordon-Kamm, Sep. 13, 2011.
"Study of tissue culture of immature embryos and plant regeneration in maize," Journal of Sichuan University (Natural Science Edition), 36:1125-1126, Abstract, 1999. (English Translation).
Svab et al., "Aminoglycoside-3—adenyltransferase confers resistance to spectinomycin and streptomycin in nicotiana tabacum," Plant MoL Biol., 14:197-205, 1990.
Svab et al., "High-frequency plastid transformation in tobacco by selection for a chimeric aadA gene," Proc. Natl. Acad. Sci. USA, 90:913-917, 1993.
Tang et al., "Regeneration of transgenic loblolly pine (*Pine taeda* L.) from zygotic embryos transformed with Agrobacterium tumefaciens," Planta, 213:981-989, 2001.
Topfer et al., "Uptake and transient expression of chimeric genes in seed-derived embryos," The Plant Cell, 1:133-139, 1989.
Trick et al., "SAAT: sonication-assisted agrobacterium-mediated transformation," Transgenic Research, 6:329-336, 1997.
Vertucci et al., "Theoretical basis of protocols for seed storage," Plant Physiology, 94:1019-1023, 1994.
Von Post et al., "A high-throughput DNA extraction method for barley seed," Euphytica, 130:255-260, 2003.
Wang et al., "Maize (*Zea mays*) genetic transormation by co-cultivating germinating seeds with agrobacterium tumefaciens," Biotechnol. Appl. Biochem., 46:5155, 2007.
Wilcox, "Soybeans: Improvement, Production, and Uses," American Society of Agronomy, Crop Science Society of America, Soil Science Society of America, 1987.
WPI Week Database No. TW558420, dated Oct. 21, 2003.
Xue et al., "A multi-needle-assisted transformation of soybean cotyledonary node cells," Biotechnol. Lett., 28:1551-1557, 2006.
Zambre et al., "Light strongly promotes gene transfer from agrobacterium tumefaciens to plant cells," Planta, 216:580-586, 2003.
Office action dated Mar. 9, 2012, in European Patent Application No. 08731808.5.
Information Disclosure Statement filed for U.S. Appl. No. 12/045,498 on Apr. 28, 2008.
Information Disclosure Statement filed for U.S. Appl. No. 12/045,498 on Aug. 14, 2008.
Information Disclosure Statement filed for U.S. Appl. No. 12/045,498 on Oct. 20, 2008.
Information Disclosure Statement filed for U.S. Appl. No. 12/045,498 on Oct. 6, 2011.
Notice of Allowance regarding U.S. Appl. No. 10/710,067, dated Jan. 29, 2008.
Notice of Allowance regarding U.S. Appl. No. 11/054,330, dated Dec. 12, 2008.
Notice of Allowance regarding U.S. Appl. No. 11/613,031, dated Sep. 16, 2010.
Notice of Allowance regarding U.S. Appl. No. 12/047,198, dated Oct. 1, 2009.
Notice of Allowance regarding U.S. Appl. No. 12/047,212, dated Oct. 1, 2009.
Notice of Allowance regarding U.S. Appl. No. 12/047,212, dated Mar. 1, 2010.
Notice of Allowance regarding U.S. Appl. No. 12/192,932, dated Aug. 15, 2010.
Office Action regarding Brazilian Application No. PI0513090-5, dated Aug. 23, 2016.
Harrell et al., "Automated, in vitro harvest of somatic embryos," Plant Cell, Tissue and Organ Culture 39:171-183, 1994.
Perry et al., "Rapid isolation of *Arabidopsis thaliana* developing embryos," BioTechniques 35:278-282, 2003.
Weitbrecht et al., "First off the mark: early seed germination," J of Experimental Botany; 62. No. 10:3289-3309, 2011.
Office Action regarding Brazilian Application No. PI0808716-4, dated Feb. 9, 2017.
Barros et al., "TRANSFORMAcA0 Genetica de Coffea arabica Atraves de Bombardeamento," Biotecnologia pp. 150-152, 2000.
Abdelnour-Esquivel et al., "Cryopreservation of Zygotic Embryos of *Coffea* ssp.," Cryo-Letters 13:297-302, 1992.
Cho et al., "Transformation of recalcitrant barley cultivars through improvement of regenerability and decreased albinism," Plant Science 138:229-244, 1998.
Cho et al., "High-frequency transformation of oat via microprojectile bombardment of seed-derived highly regenerative cultures," Plant Science 148:9-17, 1999.
Cho et al., "Production of transgenic tall fescue and red fescue plants by particle bombardment of mature seed-derived highly regenerative tissues," Plant Cell Reports 19:1084-1089, 2000.
Cho et al., "Transformed $T_0$ orchardgrass (*Dactylis glomerate* L.) plants produced from highly regenerative tissues derived from mature seeds," Plant Cell Reports 20:318-324, 2001.
Cho et al., "Stable transformation of rice (*Oryza sativa* L.) via microprojectile bombardment of highly regenerative, green tissues derived from mature seed," Plant Cell Reports 22:483-489, 2004.
Ha et al., "Stable Transformation of a Recalcitrant Kentucky Bluegrass (*Poa pratensis* L.) Cultivar Using Mature Seed-Derived Highly Regenerative Tissues," In Vitro Cell. Dev. Biol.—Plant 37:6-11, 2001.
Higley et al., "Effects of non-destructive tissue extraction on the viability of corn, soybean, and bean seeds," Seed Sci. & Technol. 22:245-252, 1994.
Li et al., "The Level of Expression of Thioredoxin is Linked to Fundamental Properties and Applications of Wheat Seeds," Molecular Plant 2:430-441, 2009.

(56) References Cited

OTHER PUBLICATIONS

Zhang et al., "Transformation of recalcitrant maize elite inbreds using in vitro shoot meristematic cultures induced from germinated seedlings," *Plant Cell Reports* 21:263-270, 2002.
U.S. Appl No. 15/826,540, filed Nov. 29, 2017, Dersch et al.
U.S. Appl. No. 16/553,911, filed Aug. 28, 2019, Adams et al.

\* cited by examiner

PREPARATION AND USE OF PLANT EMBRYO EXPLANTS FOR TRANSFORMATION

CROSS REFERENCE TO RELATED APPLICATIONS

This application is a continuation of U.S. application Ser. No. 14/642,671, filed Mar. 9, 2015, which is a continuation of U.S. application Ser. No. 13/750,977, filed Jan. 25, 2013, now issued as U.S. Patent 9,006,513, which is a continuation of U.S. application Ser. No. 12/045,498, filed Mar. 10, 2008, now issued as U.S. Patent 8,362,317, which claims the priority of U.S. Provisional application Ser. Nos. 60/894,096, filed Mar. 9, 2007, and 60/915,066, filed Apr. 30, 2007, the entire disclosures of which are incorporated herein by reference in its entirety.

BACKGROUND OF THE INVENTION

1. Field of the Invention

The invention relates generally to methods for preparing and storing embryonic plant tissue and its subsequent use in regeneration and transformation. The invention relates generally to methods for preparing and storing embryonic plant tissue directly from dry seed and its subsequent use in regeneration and transformation. The resulting novel explant is storable and can germinate and or be transformed when appropriate conditions are provided.

2. Description of Related Art

Transformed plants may be obtained by directly treating meristematic tissue of a plant embryo (e.g. U.S. Pat. No. 6,384,301). The meristematic tissue contains formative plant cells that differentiate to produce multiple plant structures including stem, roots, leaves, germ line tissue, and seeds. Plant embryos may be treated and selected or screened to determine which of those treated embryos have incorporated the new genetic information into germ line tissue. U.S. Pat. Nos. 6,384,301 and 7,002,058 and U.S. Publication 20060059589 describe methods of genetically transforming soybeans (*Glycine max*) using bacterial-mediated gene transfer directly on the meristematic cells of soybean embryos.

In typical soybean transformation procedures, seeds are hydrated/imbibed to soften the seed coat and allow for or extraction of the explant tissue. After hydration the embryo or embryonic tissue is excised from seed. When meristems are used as the explant, primary leaf tissue may be removed to expose the meristem of the soybean embryo. Considerable effort is involved in excising the embryos, transferring the genetic material into the embryos, and culturing the embryos. Processing can cause damage to the explant tissue, which negatively impacts subsequent transformation and regeneration steps. It is thus important to reduce damage to the explant tissue that could result in transformation and/or regeneration effort being applied to non-viable tissue.

The excision of plant embryos is often therefore performed by hand. In this process, surface sterilized seeds are aseptically handled one at a time with gloved hands. The explant is then carefully excised. In the case of meristems, the seeds are carefully oriented in a manner as to eject the seed coat with applied force and then the embryonic leaves (cotyledons) are removed near the primary meristem to leave the seed embryo containing meristematic tissue. Even the careful handling of individual seeds, however, results in less than desirable recovery of viable embryos, and may be less than 70% even with high quality seeds.

Bacterial contamination of embryos after excision is also a significant concern. The increased handling to preserve higher viability and recovery of explants also increases the likelihood of destructive contamination (which will manifest itself in subsequent processing steps). Such contamination can result in significant loss, as a single contaminated explant will contaminate other samples during tissue culture. This causes loss of yield and/or transformation frequency, and eventually transformation efficiency. Moreover, the manual excision is extremely labor intensive, time-consuming, and stands as a barrier to a scaling up of the transformation process in which many plants must typically be treated to yield desired results.

In addition, the current processes are limited because the harvested explant must be moved quickly into the subsequent steps of transformation, or viability is lost. Typically, once an explant is harvested (e.g. U.S. Patent Application Publication 20050005321 and corresponding PCT Publication WO 2005/000471), it is placed on media and subjected to co-culture with transforming bacteria within hours of being removed. Thus, anytime transformations are to be performed, it is necessary to first prepare all of the explants that will be needed so they are ready to immediately move into an incubation or transformation process. This timing can be very complicated and inflexible, particularly if sudden demands arise and explants cannot be prepared in time. Clearly, the lack of an ability to store such explants for more than a few hours is a major deficiency in the art.

There remains a great need for processes that can increase the availability of transformable embryos without unacceptably increasing total costs and/or timelines of explant preparation for transformation. The ability to store excised meristematic tissue (explant) for later use in particular has been lacking. Such methods would substantially increase the availability of transformable embryos, and allow efficient planning and execution of large-scale transformation studies. Such methods should enable explant storage to meet demands created during peak operational hours or during inadvertent disruptions in the production line and shipping of explants, for example, to different sites for maintaining production runs. Further, the use of dry embryo explants (artificial seeds) for transformation is not known in the art due to common wisdom in the art to use "wet" explants for transformation.

SUMMARY OF THE INVENTION

In one aspect, the invention provides a seed explant having a specified moisture content. In one embodiment, an explant may comprise an internal moisture content of from about 3% to about 20%. In a further embodiments, an explant provided herein may be defined as a storable, substantially intact embryo axis containing at least some meristem tissue that is extracted from a seed with an internal moisture as specified herein, for example, from about 3% to about 20%.

In another aspect, the invention comprises a method for producing obtaining a plant comprising the steps of: (a) obtaining a dry plant seed; and (b) preparing an explant from the plant seed under conditions wherein the explant does not germinate and remains viable and competent for germination and or genetic transformation. The plant seed may be a soybean, canola, corn, cotton, onion, pepper, tomato, cucurbit, rice, or wheat seed.

In certain embodiments, the explant comprises a substantially intact seed modified to expose at least a first transformable cell of the seed. In other embodiments, the method for preparing the explant may comprise drilling at least a first aperture in the seed, or nicking the seed. The seed or explant comprises meristematic tissue.

In certain embodiments the method may further comprise the step of (c) transforming at least a first cell of the explant with a selected DNA, and (d) regenerating a transgenic plant from said cell, wherein the regenerated plant is stably transformed with the selected DNA. Regenerating may be performed at a temperature of up to about 35° C. The explant may further comprise meristematic tissue, for instance an embryonic meristem. In one embodiment, a plant may be regenerated without the use of one or more plant growth regulators such as to alter the development of the explant.

In other embodiments, the method may comprise storing the explant prior to step (c) or (d) under conditions wherein the explant does not germinate. In yet other embodiments, the seed or explant may be dehydrated prior to or after preparing the explant. A transformable and regenerable explant produced by the method is also an aspect of the invention.

In certain embodiments, the conditions in step (a) or (b) may comprise a seed or explant internal moisture content of from about 3% to about 25%. In particular embodiments the conditions in step (a) or (b) may comprise a seed or explant moisture content of from about 4% to about 16%. In certain embodiments, the method may be defined as comprising reducing the moisture content of the plant seed and/or the explant prior to step (c). In other embodiments, the method may further be defined as comprising increasing the moisture content of the explant prior to, concurrently with, and/or after step (d).

Further, the methods may be defined as ones wherein step (a) and/or step (b) is performed in the absence of a liquid. Alternatively, the methods may be defined as ones wherein step (a) and/or step (b) is performed in the presence of a liquid. In yet other embodiments, the methods may be defined as ones wherein step (a) and step (b) are performed in the absence of a liquid. The conditions in step (a) or (b) may comprise a temperature of between about −80° C. and about 60° C. In particular embodiments, the temperature may be between about −20° C. and about 40° C.

In other embodiments, the method may be defined as one wherein step (b) is further defined as comprising obtaining a plurality of explants from plant seeds and selecting an explant from the plurality based on a characteristic associated with the ability to transform the explant and/or regenerate a plant from the explant. In particular embodiments, the characteristic is selected from the group consisting of color, size, shape, density, proximate analysis, carbohydrate content, protein content, fat content, volatile content, fibre (ash) content, moisture content, viability, germplasm, intactness, pathogen presence, and optical characteristics.

In certain embodiments, the method may be further defined as comprising sanitizing the plant seed and/or the explant prior to or concurrently with step (c). The method may further comprise priming the seed by contacting the seed with an aqueous solution. The aqueous solution may comprise a disinfectant such as bleach or alcohol. The method may further be defined as comprising disinfecting the plant seed and/or the explant prior to step (c). In certain embodiments, the method may comprise disinfecting the explant, wherein disinfecting comprises application of a disinfectant selected from the group consisting of bleach, alcohol (e.g. ethanol), ozone, chlorine gas, ultraviolet light, temperatures of −20° C. or lower, and exposure to a temperature higher than 40° C. or 50° C.

The method for obtaining an explant from a seed may be automated. In certain embodiments, the method comprises an automated process in which the plant seed is oriented as it passes through a mechanical separator to provide a substantially uniform output of regenerable meristematic plant tissue. The method may be performed on bulk seed using the force generated with opposing rollers, such as illustrated in FIG. 6, for example, as well as on singulated seed such as illustrated in FIGS. 2-5, for example.

In some embodiments, the transformation method may be carried out by bacterially-mediated transformation, or by microprojectile bombardment. Explant transformation may be carried out prior to, or subsequent to, explant disinfection. The method may be performed wherein the transgenic plant is regenerated without producing a callus tissue culture, by organogenesis or by direct meristem transformation and subsequent shoot growth.

Further, the method may comprise storing the explant for from about 1 hour to about 2 years prior to step (c) or step (d). In certain embodiments the method may comprise storing the explant for from about 1 hour to about 24 hours. The explant may be hydrated or pre-cultured after storage.

Another aspect of the invention comprises an apparatus for preparation of transformable embryonic plant tissue from singulated seed comprising: (a) a holder for a singulated seed; (b) means for applying a force to the seed being held so as to divide the seed into separate cotyledons, seed coat and embryonic tissue. The apparatus may further comprise: (c) a means for separating the embryonic tissue from the seed coat and cotyledons and (d) a means for cleaning and/or sterilizing the tissue. FIGS. 2-5 illustrate an apparatus for preparation of transformable embryonic plant tissue from singulated seed. As shown in FIG. 3, the apparatus (1) comprises a holder (2) for the singulated seed (16). As shown in FIG. 2, the holder (2) comprises an upper and lower seed fixture (3, 4); and means for applying force to the seed (16) at a shear force point or plane (5), to divide the seed (16) into separate cotyledons, seed coat, and embryonic tissue. The holder may comprise vacuum cups (6) that maintain the position of the seed (16) while applying a shear force to it. FIG. 4 illustrates an alternative embodiment of the holder (2), wherein serrated knurled posts (7) maintain the position of the seed (16) while applying shear force. The vacuum cups or serrated posts turn in opposite directions, generating the force which results in division of the seed (16) at or near the shear force point (5). The apparatus further comprises vacuum generators (8) or similar means for removing components of a sheared singulated seed from the vicinity of the holder (2), allowing the next seed to he placed therein.

FIG. 6 illustrates a method useful for bulk separation of embryonic meristem tissues from cotyledon tissue and seed coat tissues. Sheer is generated between rollers. In this example, one is metal and one is an elastomer. Dry seed is passed between these two rollers at a gap setting appropriate for the seed type, and sheer is applied such that the seed is split and seed coats and cotyledon parts can be further separated from the desired meristem containing embryo axis, for example, utilizing adjustable air flow and properly sized screens or the like.

FIG. 7 illustrates an apparatus for separating embryonic tissue from cotyledon, seed coat, or other debris, and cleaning the tissue. As shown in the separator (13) of FIG. 7, sterile air flows through a manifold (9) into an explant delivery and recovery chamber (10). Air flow forces the plant material comprising embryonic tissue into an explant free flight area (11), where materials are separated. The apparatus may further comprise an explant excluding chamber (12) to prevent explant loss but allow passage of dust and airflow out of the separator (13), and anmeans for static removal such as an ion generator (17). FIG. 8 illustrates an alternative embodiment of the separator (13), comprising charged plates (14) to collect dust, mold spores, or the like. FIG. 9 illustrates yet another embodiment of a separator, further comprising a means for sterilizing the tissue. As shown in FIG. 9, a sterilizing means such as germicidal UV lamps (15) may be placed within the separator (13), such as within the explant free flight area (11), to sterilize the explant tissue.

Still yet another aspect of the invention is a method for preparing transformable and regenerable explant material comprising meristematic tissue from a singulated seed, comprising: a) subjecting a singulated seed that comprises a seed coat, cotyledon tissue, and meristematic tissue to a force sufficient to fracture the seed; and b) separating the meristematic tissue from the seed coat and optionally the cotyledon tissue, wherein the method is mechanized. A transgenic plant produced by this method, wherein the method further comprises transforming and regenerating the explant material to produce a transgenic plant, is also an aspect of the invention. In certain embodiments the plant may be a soybean, cotton, onion, pepper, rice, wheat, cucurbit, canola or corn plant.

BRIEF DESCRIPTION OF THE DRAWINGS

The following drawings are part of the present specification and are included to further demonstrate certain aspects of the present invention. The invention may be better understood by reference to the drawings in combination with the detailed description of specific embodiments presented herein.

DETAILED DESCRIPTION OF THE INVENTION

Figure 1:
FIG. 1: Yield of meristematic soybean explants after subjecting seeds to automated excision.

The following is a detailed description of the invention provided to aid those skilled in the art in practicing the present invention. Those of ordinary skill in the art may make modifications and variations in the embodiments described herein without departing from the spirit or scope of the present invention.

The invention provides methods and compositions for preparing and recovering and storing explants, for instance, using mechanization and automation. Fluid can be used to move explants and separate desirable explants from debris during mechanized handling of seeds and embryonic tissue, including compressed air, other gases, and liquids. Wet or dry excision of plant embryos to yield transformable meristematic tissue may be performed, followed by immediate use in transformation methods. Alternatively, wet or dry excised embryos may be subsequently dried and stored for later transformation or other use and dry excised embryos may be stored as such or after drying them further depending upon their moisture content at the time of excision.

Flexibility of plant transformation methods is increased by redefining the storage product from seed to transformation-ready explant. Explant preparation can occur at off-peak times and days, and explants stored for later use, greatly enhancing the efficiency of the overall transformation process. Advancements in excision, processing, explant isolation and storage, and manipulation make this process much more labor efficient and well suited for high volume, high-throughput transformation needs. Methods for the manipulation of the moisture content of the seed to adjust seed shattering characteristics and subsequent seed and explant vigor and process yield are also provided by the invention. Transformable embryos and meristems produced by the described methods are further an embodiment of the invention.

In one embodiment, an explant prepared in accordance with the invention may be defined as having an internal moisture of about 4-25%, including about 4, 5, 6, 7, 8, 9, 10, 11, 12, 13, 14, 16, 17, 18, 19, 20, 21, 22, 23, 24, and 25% internal moisture, and specifically including all ranges derivable between any two such values. In particular embodiments, seeds from which explants are to be prepared may be harvested at a predetermined internal moisture suitable for isolating transformable material therefrom. In certain non-limiting embodiments, seeds from which explants are obtained may be defined as having an internal moisture of about 3-25%, including about 3, 4, 5, 6, 7, 8, 9, 10, 11, 12, 13, 14, 16, 17, 18, 19, 20, 21, 22, 23, 24, and 25% internal moisture, and specifically including all ranges derivable between any two such values, such as, for example, from about 4% to 16%. In certain embodiments, brittleness of seeds may be altered by manipulating moisture content, allowing for efficient splitting of seeds and preparation of explants. For instance, an internal moisture content such as 3% to 7% may be advantageous. Seeds may be held at such moisture contents or any other moisture content yielding stable storage conditions (and transformable explants) prior to use. The seeds in certain embodiments may be soybean or cotton seeds, and may also be, without limitation, corn, canola, onion, pepper, tomato, cucurbit, rice, common bean, peanut, maize, wheat, or rapeseed seeds.

Dry explants may be used that have been excised from seed under low moisture conditions, and may be prepared as dried wet explants by excising from seed following hydration/imbibition where the explant is subsequently dehydrated and stored, including combinations thereof. The explants may be of various ages. In one embodiment, explants are relatively "young" in that they have been removed from seeds for less than a day, for example, from about 1 to 24 hours, such as about 2, 3, 5, 7, 10, 12, 15, 20, or 23 hours prior to use. In other embodiments, explants may be stored for longer periods, including days, weeks, months or even years, depending upon storage conditions used to maintain explant viability. Those of skill in the art in particular will understand that storage times may be optimized such that the quality and/or yield of transformants as well as the efficiency of the transformation process is maximized. This can be carried out for any particular transformation protocol, for example, such as *Agrobacterium*-mediated transformation, microprojectile bombardment transformation, as well as other transformation procedures.

Prior to embryo excision, seeds may be subjected to an optional culling step intended to remove seeds with a high degree of bacterial or fungal contamination and also seeds that may for any reason would be unlikely to produce viable embryonic tissue for use with the present invention. Culling may be carried out, for example, based on parameters such as the size, color, or density of the seed or other physical characteristics that in other contexts would be unobjectionable, and may be adjusted empirically by variation of the excision, sterilization, and storage parameters and by measurement of ultimate yields of viable tissue and of regeneration and transformation efficiencies. Examples of culling methods may include the use of an automatic scale after size sorting. An optical sorter suitable for this purpose is the Sortex Seed Sorter or the Satake ScanMaster™ II (Satake USA Inc., Houston, Tex.). Other culling techniques may also be employed including culling by moisture content.

In certain embodiments of the invention, recovered dry explants may be washed prior to use in a fluid, which can be a gas or liquid. An example of use of a gas includes flushing dry explants in sterile air while de-ionizing explants to remove static. Further, specifically charged plates and UV germicidal lamps can be used to remove undesirable particles such as contaminants and microscopic dust. Dry explants may also be subjected to a hydration (pre-culture) to increase internal moisture content prior to being transformed with a heterologous nucleic acid. Transformation is alternatively carried out prior to priming or germination. In this embodiment, seed and/or explant sterilization is carried out, e.g., using Cl gas, followed by chipping or breaching of the seed protective outer skin by other means, allowing infiltration of a liquid *Agrobacterium* culture. This process can be carried out immediately following the sterilization and breaching of the seed coat, or after continued storage.

The invention may in particular aspects involve sterilization of explants prior to excision and/or post-excision. Sterilization can include contacting seed or explant material with various fluids (i.e. liquid or gaseous) that serve to reduce or eliminate the presence of viable bacterial or fungal contaminants that could otherwise interfere with seed or embryo viability and later plant tissue culture. Sterilization by application of liquid may also hydrate or partially hydrate the plant tissues, and serve the purpose of priming seeds or embryos. Methods for sterilization include, but are not limited to, use of chlorine gas, ozone, solutions of bleach or alcohol, ultraviolet light, temperatures of −20° C. or lower, and exposure to a temperature higher than 40° C.

Splitting of seeds to isolate the explant may be performed manually or by an individual using a variety of mechanical techniques in order to isolate the explant. Seeds may be split in half along the axis of the cotyledon, using tools such as forceps or by hand. For instance, a seed may be split or fractured along the axis of the cotyledon by applying direct pressure to the seed along the same axis. This may be accomplished, for example, by striking the seed with a hard object, or by using a press, such as a standard arbor press (e.g. Dayton 4Z328A or Dayton 4Z329D; Dayton Tool Company, Dayton, Ohio). Some seeds will split such that the explant may be immediately separated. Other seeds may split along the axis of the cotyledon, but may still require additional manipulation to isolate the explant. Automated mechanical excision of hydrated embryo tissue comprising meristems may also be attempted by putting seeds through counter rotating cylinders and collecting resulting seed material, for instance as is described in U.S. Patent Publication 20050005321.

In some embodiments, a dry seed or an explant may be first primed, for example, by imbibition of a liquid such as water or a sterilization liquid, redried, and later used for transformation and regeneration. In other embodiments, the seed or the explant may be primed by raising the internal seed moisture content to greater than 30%, holding the seed or the explant at a time point, and then re-initiating imbibition at a later time point. In an alternative embodiment, the seed or the explant may be primed by raising the internal moisture content to greater than 30%, storing the seed or the explant for a predetermined period, drying the seed or the explant to the internal moisture content of below 20%, and then re-initiating imbibition.

In another embodiment of the invention, explant quality yield can be optimized by pre-orientation of seeds prior to seed disassembly. In this manner, the relatively random impact of the seeds hitting a roller in an automated machine is controlled, thus controlling the splitting of the seeds between the cotyledon halves.

Figure 4:
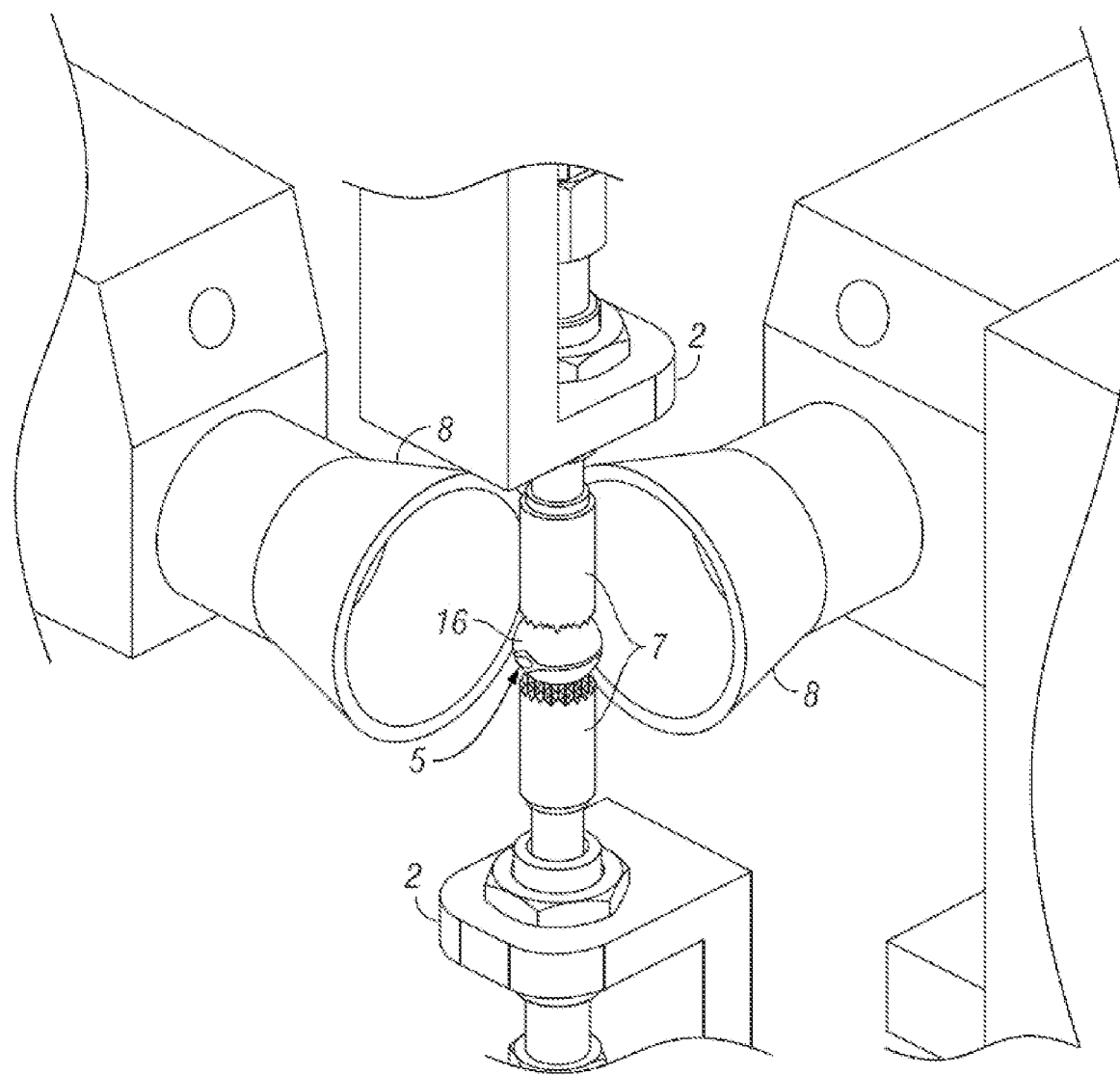
FIG. 4: Partial perspective view of apparatus (FIG. 5) for high throughput explant excision from single seed using serrated seed holder.
Figure 5:
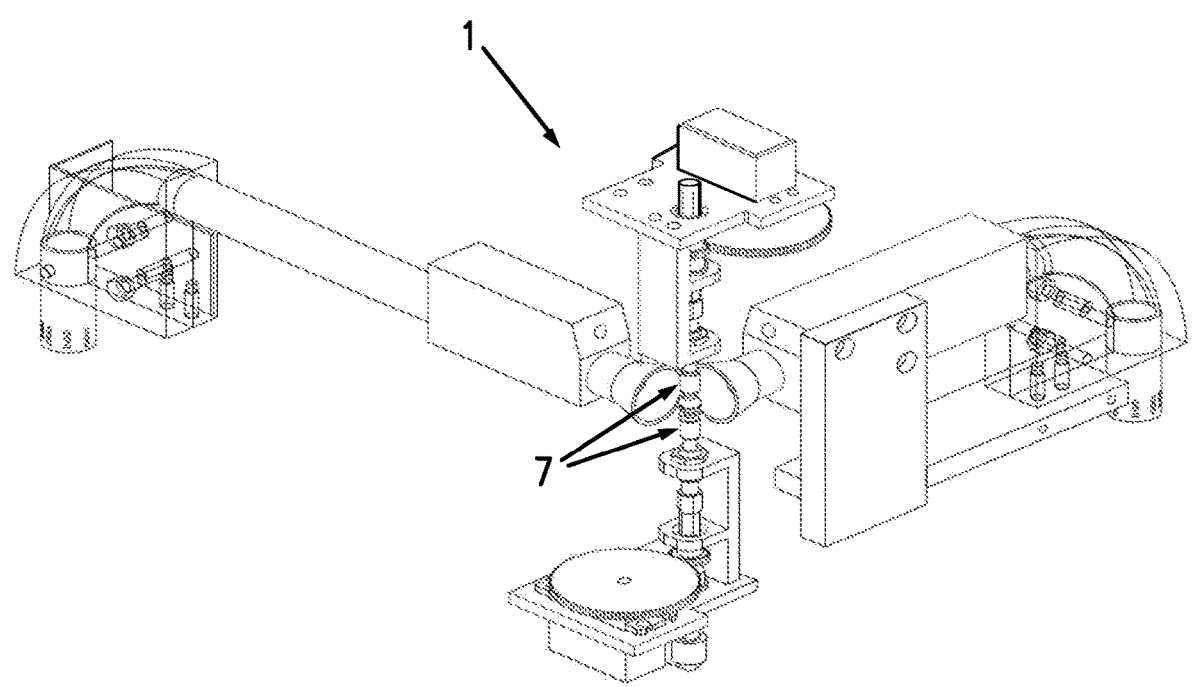
FIG. 5: Simplified representation of an apparatus with serrated seed holder for the excision of explant material from singulated seed.
Figure 6:
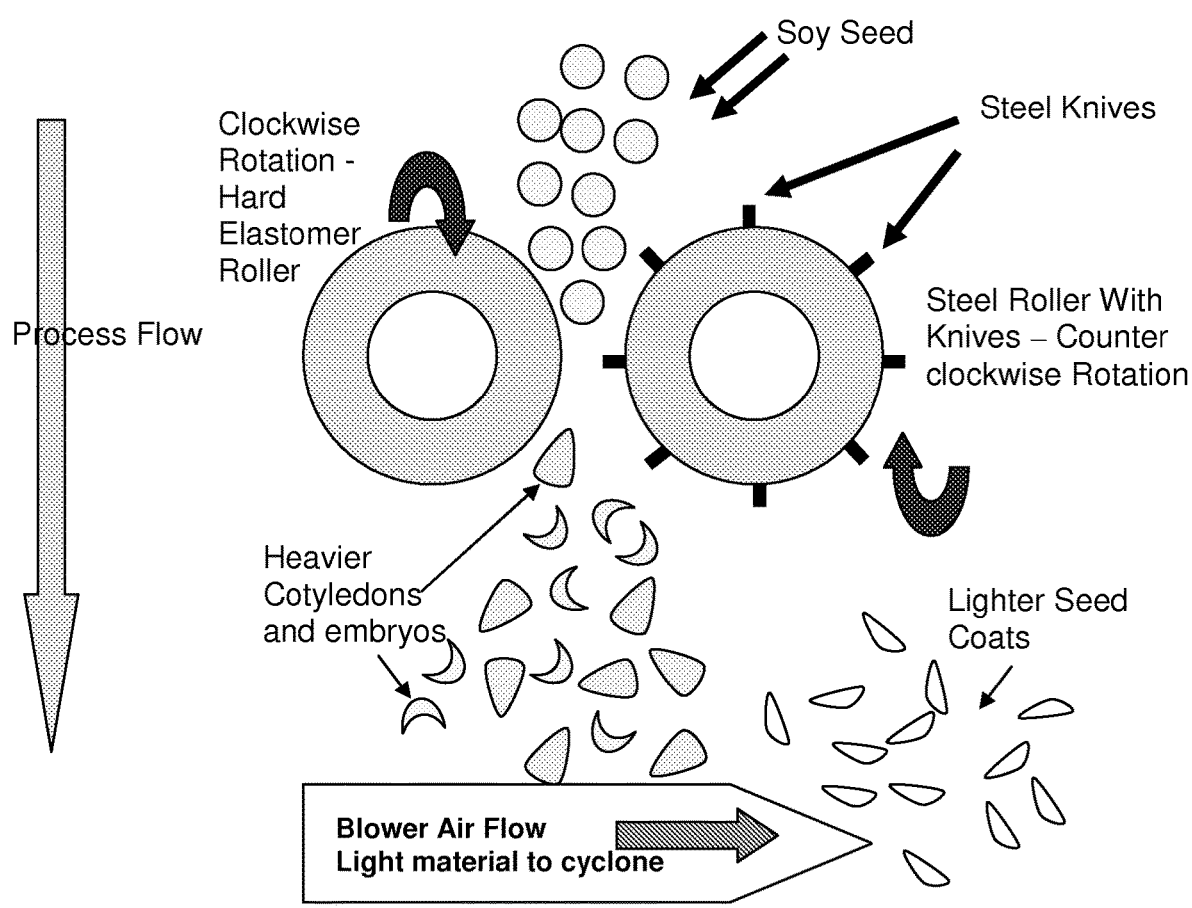
FIG. 6: Flow chart showing principal steps of the Excision Process.

Any method to separate desired explant material from individual split seeds or the bulk yield of split seeds may be used (e.g. a process as shown in FIG. 6, or use of an apparatus as shown in FIGS. 2-5 and FIGS. 10-11), for instance by automated processing. Such methods may include aspiration in which a partial vacuum is applied to a first chamber containing bulk yield from the rice shelter or other machine. The first chamber consists of a series of alternating angled sides. As seed material falls down these sides and into a collection vessel, vented slots in the chamber allow lighter material to be pulled into a second chamber. Airflow, and thus the weight of the seed material being pulled through, is controlled by valves. FIG. 6 describes an exemplary automated process for excising and separating explant material from seed coats and other tissues. Following excision the excised explant may then be stored under appropriate temperature and moisture conditions for later use.

In another embodiment of the invention, rather than performing excision of bulk seed, seeds are singulated prior to explant excision, and excision is performed on the singulated seed, for instance, via a high throughput method (e.g. FIGS. 2-5). The seed (e.g. a soybean seed) may be manipulated by a vacuum cup system to locate the seed, and then placed between holders such as a set of vacuum cups or serrated surfaces. In a particular embodiment the seed coat is removed by use of a blast of high pressure air or other fluid, or particles, to pulse or blast the seed coat from the seed. The seed tissue may then be manipulated and placed into a suitable container for further manipulation, such as embryo excision, culling, processing, storage, and transformation. In another embodiment, culling, selection, or other processing steps may occur prior to seed singulation. The singulated seed may be at a predetermined moisture level, for instance as determined by storage conditions following seed harvest. The singulated seed may be automatically imaged for analysis of pre-determined quality, for instance, to test for viability, chemical and biological properties, and suitability in the transformation or regeneration process. The excised explant may be stored under appropriate temperature and moisture conditions for later use. An apparatus for high throughput excision of transformable meristematic tissue from singulated seed is also an embodiment of the invention (e.g. FIGS. 2-5).

Another method for separating explant material is by manual sieving. Bulk yield from the rice Sheller or other machine is put through a series of geological separation sieves, such that unwanted large and small debris are separated from the desired explant by size exclusion. This is effectively accomplished, for instance with soybean material, using U.S. Standard sieves (listed from top to bottom): #7 (2.8 mm opening), #10 (2.0 mm opening), #16 (1.18 mm opening), and then a collection pan on the bottom. Large debris collected on either the #7 or #10 sieves, while desired embryo explant material is retained and collected on the #16 sieve. Unwanted fine particles passed through to the collection pan. The explant yield collected on the #16 sieve may be further purified by placing this yield into a vertical airflow separation column (e.g. an OREGON SEED BLOWER; Hoffman Manufacturing, Jefferson, Oreg.) in which air is passed through the material, blowing lighter unwanted material upward where it is trapped for removal. Modification of the column with various static reduction means would allow for dust removal from embryo surfaces and reduce biocontamination and remove any unnecessary plant cell and tissue.

Mechanized sieving and airflow separation may also be utilized. For instance, bulk yield from the Rice Sheller is fed into a machine that utilizes vibration and gravitational pull to sieve and separate the unwanted seed material from the desired explants. As an example, the CLIPPER OFFICE TESTER ((Tipper Separation Technologies; A.T. Ferrell Company, Bluffton, Ind.) may be utilized. This machine has two slots for separation screens to be inserted, whereby seed material is separated according to size. In addition, this machine utilizes a fan that duplicates the function of the previously mentioned vertical airflow separation device, thus giving a final purified yield of explants (FIG. 1) in a single step.

Figure 9:
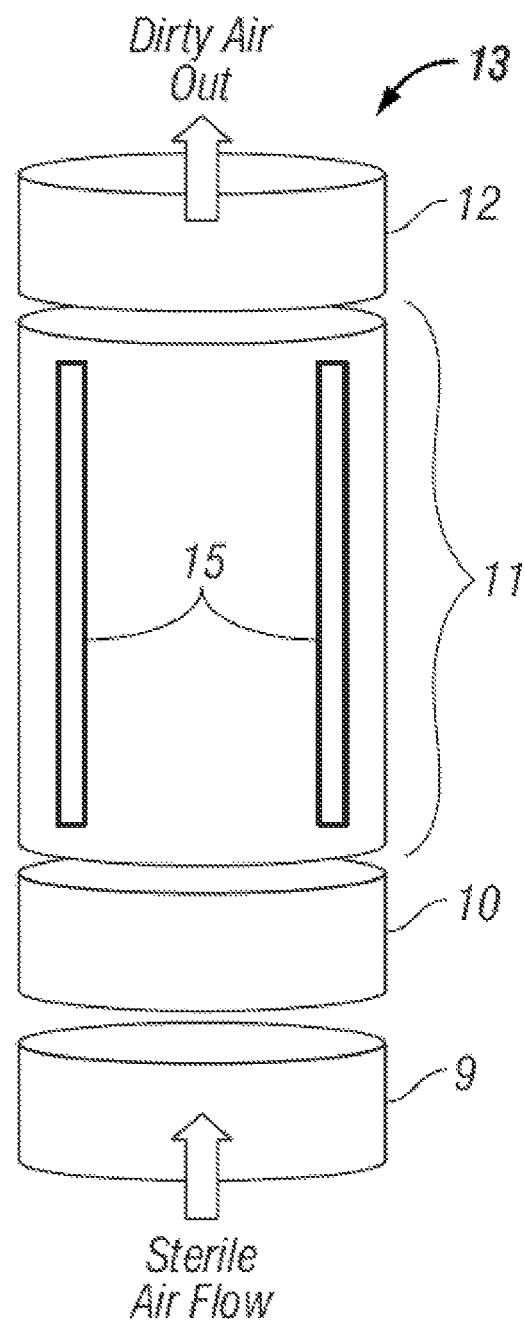
FIG. 9: Dry Explant Sanitizer embodiment 3.
Figure 10:
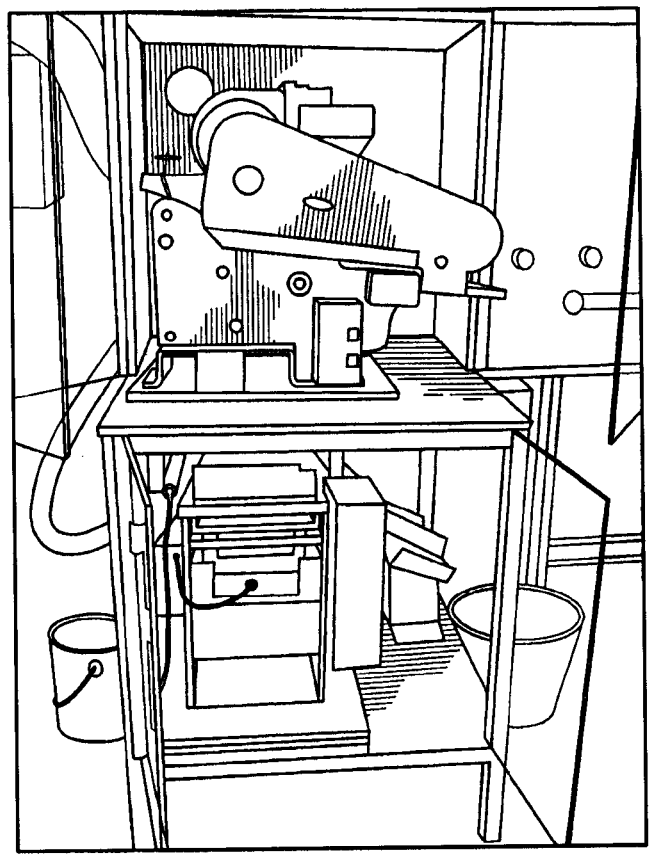
FIG. 10: Closeup view of an embodiment of a "stacked" apparatus for obtaining explant tissue from seed.
Figure 11:
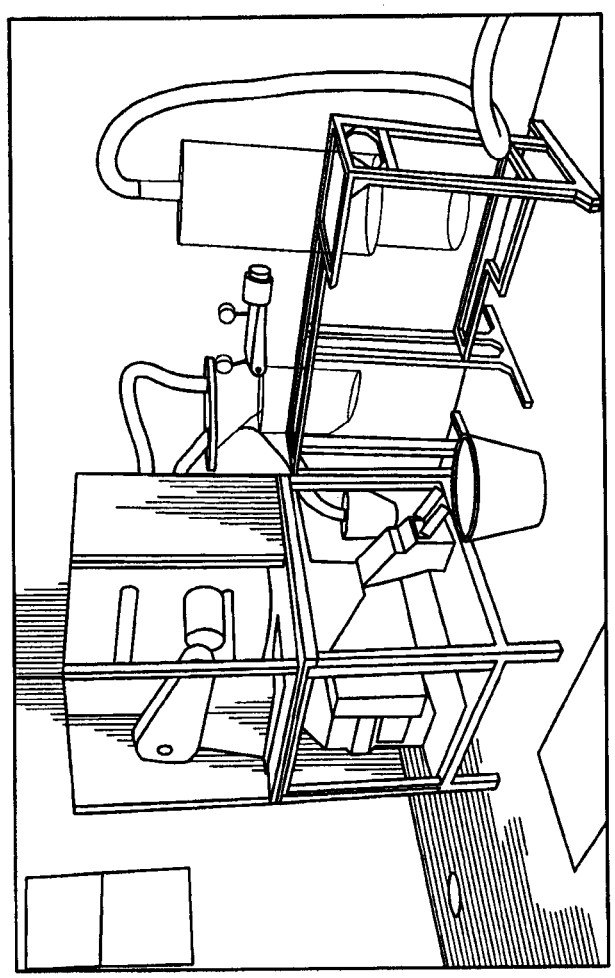
FIG. 11: Embodiment of a "stacked" apparatus for obtaining explant tissue from seed.

In one embodiment, a machine for splitting the seeds is stacked over a mechanical separator for continuous flow-through of material and for greater automation (FIGS. 10-11). The seeds are placed in the machine such as a Grainman® Laboratory Paddy Rice Sheller (e.g. Model #64-115-60-WDC; Grain Machinery Manufacturing Corp., Miami, Fla.). Much of the light material such as seed coats are separated by aspiration during the excision/splitting process (e.g. FIG. 2, FIG. 6) and the heavier seed fractions i.e., cotyledon pieces and the explants fall directly into a mechanical separator which separates the cotyledons from the explants by way of size exclusion by using vibrating sieves and gravity. Airflow is used to aspirate dust and other light seed debris out during separation (e.g. FIGS. 7-9).

Regenerable transformable explants may be harvested that contain no, some, or a part of each cotyledon remaining attached to the embryonic tissue, for example as much as ¼ of the cotyledon. These explants are considered substantially similar, as they may each result in a stable transformed plant. The explant should however contain at least some of the meristematic region of the embryo such that typically the explant can produce a shoot within 12 weeks of the onset of tissue culture growth conditions.

The explant may be recovered from a hydrated seed, from dry storable seed, from a partial hydration of dried hydrated explant, wherein "hydrating" or "hydration" is defined as any act to yield an increase in the moisture content of a seed and/or explant, without limitation as to whether or whether not the seed and/or explant being hydrated has been subject to dehydration. An explant may be from seed that is "primed"; that is, a seed that has initiated germination but has been appropriately placed in stasis pending favorable conditions to complete the germination process. Those of skill in the art will be able to use various hydration methods and optimize length of incubation time prior to transformation. The resulting novel explant is storable and can germinate and or be transformed when appropriate conditions are provided. Thus the new dry, storable meristem explant may be referred to as an artificial seed.

Examples of such hydration and priming conditions are presented below in Tables 4-8. For instance, Table 4 illustrates placing explants following excision in a 15 mL conical tube with 5 ml of sterile distilled water (SDW) for a period of 4 hours. A typical protocol for machine excision, such as the "SOP" treatment, may involve placing seeds for 15 minutes in a bleach solution of 200 ppm active Cl, followed by a 2 hour period of no liquid exposure, followed by an overnight hydration in either bean germination medium (BGM) or a bleach solution of 50 ppm active Cl.

Following excision, one of skill in the art may store the explant according to the disclosed methods prior to subsequent use. Methods and parameters for drying, storing, and germinating seed are known in the art (e.g. Senaratna et al., 1983; Vertucci and Roos, 1990; Chai et al., 1998). Storage of excised meristems in accordance with the current invention may be carried out using modifications of such storage conditions as desired. Any such conditions may be used as desired, including at temperatures, for example, of from about −80° C. to about 60° C. Temperatures of about −20° C. to room temperature in particular have been found to function well, but the invention is in no way limited to these temperatures.

The data described in the Examples illustrates, for instance, that stored seed explants comprising meristematic tissue may remain viable and useful for subsequent genetic transformation and regeneration for weeks or months following excision from seeds (e.g. Example 11 and Table 14). Manipulation of excision, sterilization, storage, hydration, redehydration, and transformation parameters allows development of efficient automated high throughput plant transformation protocols.

Figure 7:
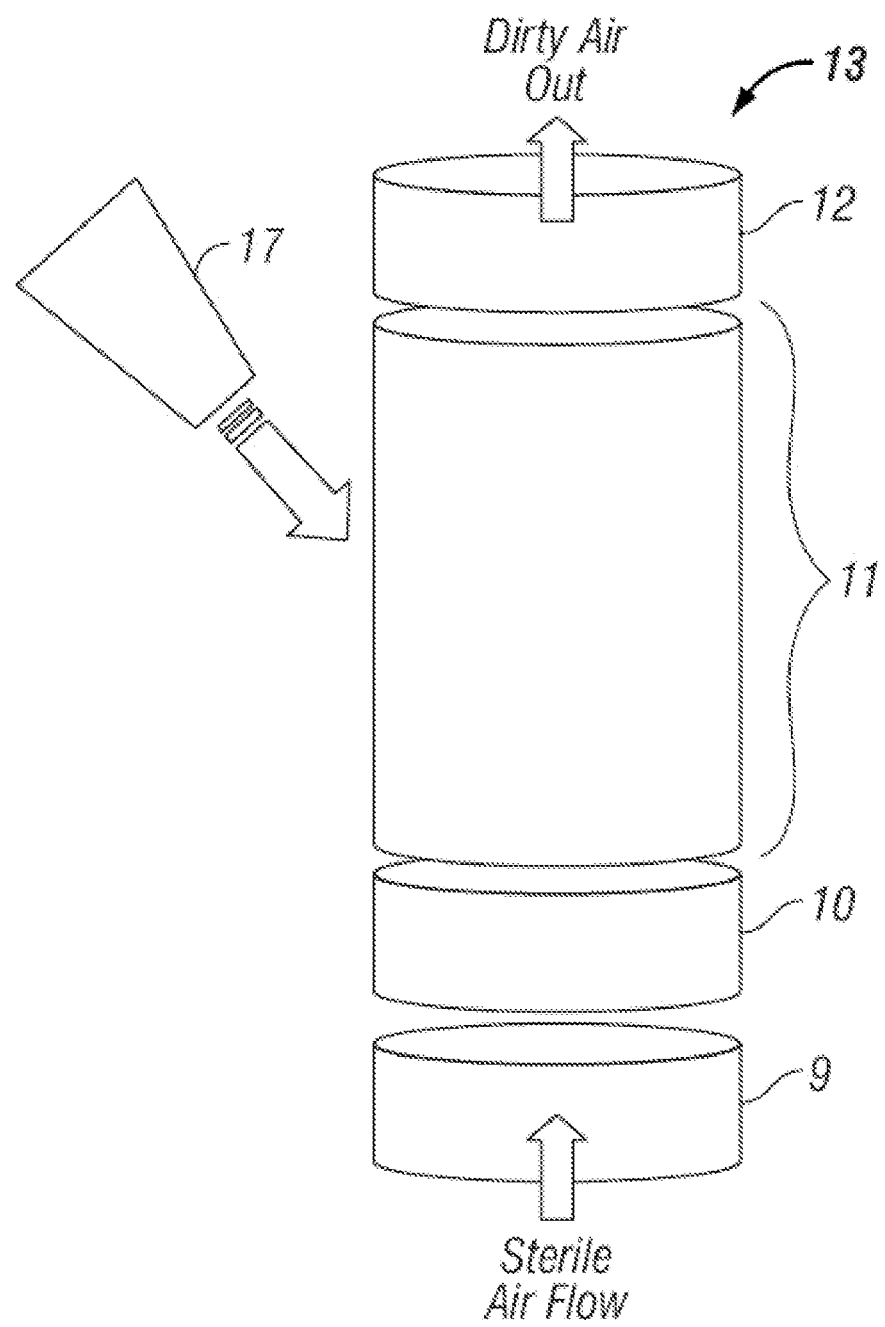
FIG. 7: Dry Explant Sanitizer embodiment 1.
Figure 8:
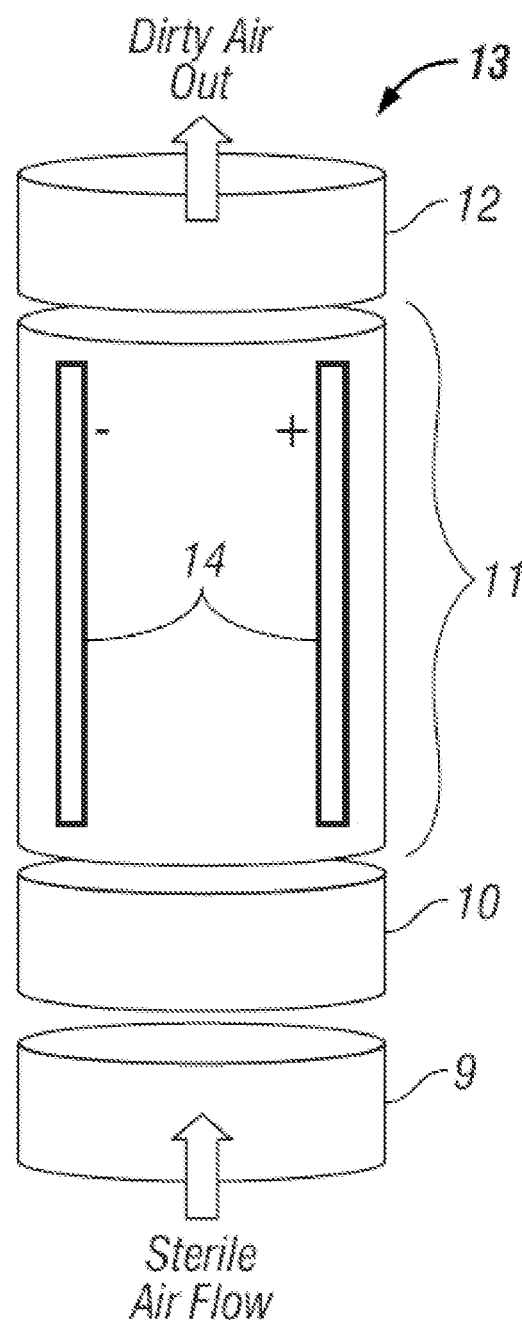
FIG. 8: Dry Explant Sanitizer embodiment 2.

A number of parameters for obtaining and handling explants may be varied. In one embodiment, the excision method may be manual; in an alternative embodiment excision occurs by an automated process. In other embodiments sterilization may be performed by contacting a seed or explant with a liquid sterilizing agent. In an alternative embodiment, a seed or an explant may be contacted with a gaseous sterilizing agent. In an alternative embodiment, a seed or an explant may be contacted with an irradiating sterilizing agent such as UV light. FIGS. 7-9 illustrate apparatuses for such sterilization methods. In an alternative embodiment, a seed or an explant may be sterilized by subjecting the seed or the explant to a brief period of high temperatures so as to reduce the vigor of biological contaminants such as adventitious bacteria and fungi on the surface of the seed or the explant without reducing the vigor of the seed or the explant. This can be achieved at a temperature higher than 40° C.; preferably the temperature is between 40° C. to 90° C. The temperature can be raised, for instance, by either forced heated air or steam. Such temperatures can be provided by dryers produced by Bry-Air Inc. (Sunbury, Ohio, USA). In still a further embodiment, moisture content of the seed at the time of excision may be varied. In another embodiment, the temperature of the seed at the time of excision may be varied. In other embodiments, a storage parameter following excision may be varied. For instance, in one embodiment the relative humidity under which explant storage occurs may be varied. In another embodiment, the explant storage temperature may be varied. In yet other embodiments, the length of explant storage time may vary. In yet other embodiments, the composition of the medium in which the explant is stored may vary. Further parameters that may be manipulated include hydration and rehydration media compositions, incubation temperature, length of time, and transformation methods, among others.

Various methods have been developed for transferring genes into plant tissue including high velocity microprojection, microinjection, electroporation, direct DNA uptake and, bacterially-mediated transformation. Bacteria known to mediate plant cell transformation include a number of species of the Rhizobiaceae, including, but not limited to, *Agrobacterium* sp., *Sinorhizobium* sp., *Mesorhizobium* sp., and *Bradyrhizobium* sp. (e.g. Broothaerts et al., 2005; U.S. Patent Application Publication 20070271627). Targets for such transformation have often been undifferentiated callus tissues, although differentiated tissue also has been used for transient and stable plant transformation.

Bacterially-mediated gene delivery (e.g. *Agrobacterium*-mediated; U.S. Pat. Nos. 5,563,055; 5,591,616; 5,693,512; 5,824,877; 5,981,840) can be made into cells in the living meristem of an embryo excised from a seed, such as soybean (e.g. U.S. Pat. No. 6,384,301). The meristematic region may be cultured in the presence of a selection agent such as the herbicide glyphosate. The result of this step is the termination or at least growth retardation of most of the cells into which the foreign genetic construction has not been delivered and the simultaneous induction of the formation of shoots, which arise from a small cluster of cells including a transformed meristematic cell. The meristem can also be cultivated in the presence of other selection agent alone or in combination, including, but not limited to auxin-like herbicides such as dicamba or 2,4-D, MCPA, glufosinate, acetolactate synthase inhibitors, protoporphyrinogen oxidase inhibitors, and hydroxyphenyl-pyruvate-dioxygenase inhibitors, neomycin, kanarnycin, paramomycin, G418, aminoglycosides, spectinomycin, streptomycin, hygromycin B, bleomycin, phleomycin, sulfonamides, streptothricin, chloramphenicol, methotrexate, 2-deoxyglucose, betaine aldehyde, S-aminoethyl L-cysteine, 4-methyltryptophan, D-xylose, D-mannose, benzyladenine-N-3-glucuronidase. Examples of various selectable markers and genes providing resistance against them are disclosed in Miki and McHugh, 2004. In one embodiment of the invention a coding region for the selectable marker aminoglycoside adenyltransferase (aadA) conferring resistance to spectinomycin or streptomycin is used (e.g. U.S. Pat. No. 5,217,902; or Sandvang, 1999).

As is well known in the art, other methods for plant transformation may be utilized, for instance as described by Miki et al., (1993), including use of microprojectile bombardment (e.g. U.S. Pat. No. 5,914,451; McCabe et al., 1991; U.S. Pat. Nos. 5,015,580; 5,550,318; 5,538,880).

Unmodified and modified protein molecules and their corresponding nucleic acid molecules providing herbicide tolerances to one or more of these herbicides are well known in the art. They are exemplified below and are incorporated herein by reference:

a) sequences encoding tolerance to glyphosate include 5-enolpyruvylshikimate-3-phosphate synthases (EPSPS; U.S. Pat. No. 5,627,061, U.S. Pat. No. RE39,247, U.S. Pat. Nos. 6,040,497, 5,094,945, WO04074443, and WO04009761), glyphosate oxidoreductase (GOX; U.S. Pat. No. 5,463,175), glyphosate decarboxylase (WO05003362 and U.S. Patent Application 20040177399), and glyphosate-N-acetyl transferase (GAT; U.S. Patent publication 20030083480) conferring tolerance to glyphosate;

b) dicamba monooxygenase (DMO, encoded by ddmC) conferring tolerance to auxin-like herbicides such as dicamba (U.S. Patent Applications 20030115626, 20030135879; Wang et al., 1996; Herman. et al., 2005);

c) phosphinothricin acetyltransferase (bar) conferring tolerance to phosphinothricin or glufosinate (U.S. Pat. Nos. 5,646,024, 5,561,236, EP 275,957; U.S. Pat. Nos. 5,276,268; 5,637,489; 5,273,894);

d) 2,2-dichloropropionic acid dehalogenase conferring tolerance to 2,2-dichloropropionic acid (Dalapon) (WO09927116);

e) acetohydroxyacid synthase or acetolactate synthase conferring tolerance to acetolactate synthase inhibitors such as sulfonylurea, imidazolinone, triazolopyrimidine, pyrimidyloxybenzoates and phthalide (U.S. Pat. Nos. 6,225,105; 5,767,366, 4,761,373; 5,633,437; 6,613,963; 5,013,659; 5,141,870; 5,378,824; 5,605,011);

f) haloarylnitrilase (Bxn) for conferring tolerance to bromoxynil (WO8704181A1; U.S. Pat. No. 4,810,648; WO8900193A);

g) modified acetyl-coenzyme A carboxylase for conferring tolerance to cyclohexanedione (sethoxydim) and aryloxyphenoxypropionate (haloxyfop) (U.S. Pat. No. 6,414,222);

h) dihydropteroate synthase (sulI) for conferring tolerance to sulfonamide herbicides (U.S. Pat. Nos. 5,597,717; 5,633,444; 5,719,046);

i) 32 kD photosystem II polypeptide (psbA) for conferring tolerance to triazine herbicides Hirschberg et al., 1983);

j) anthranilate synthase for conferring tolerance to 5-methyltryptophan U.S. Pat. No. 4,581,847);

k) dihydrodipicolinic acid synthase (dapA) for conferring to tolerance to aminoethyl cysteine (WO8911789);

l) phytoene desaturase (crtI) for conferring tolerance to pyridazinone herbicides such as norflurazon (JP06343473);

m) hydroxy-phenyl pyruvate dioxygenase for conferring tolerance to cyclopropylisoxazole herbicides such as isoxaflutole (WO 9638567; U.S. Pat. No. 6,268,549);

n) modified protoporphyrinogen oxidase I (protox) for conferring tolerance to protoporphyrinogen oxidase inhibitors (U.S. Pat. No. 5,939,602); and o) aryloxyalkanoate dioxygenase (AAD-1) for conferring tolerance to an herbicide containing an aryloxyalkanoate moiety (WO05107437). Examples of such herbicides include phenoxy auxins (such as 2,4-D and dichlorprop), pyridyloxy auxins (such as fluroxypyr and triclopyr), aryloxyphenoxypropionates (AOPP) acetyl-coenzyme A carboxylase (ACCase) inhibitors (such as haloxyfop, quizalofop, and diclofop), and 5-substituted phenoxyacetate protoporphyrinogen oxidase IX inhibitors (such as pyraflufen and flumiclorac).

A variety of tissue culture media are known that, when supplemented appropriately, support plant tissue growth and development, including formation of mature plants from excised meristems or embryos. These tissue culture media can either be purchased as a commercial preparation or custom prepared and modified by those of skill in the art. Examples of such media include, but are not limited to those described by Murashige and Skoog, (1962); Chu et al., (1975); Linsmaier and Skoog, (1965); Uchimiya and Murashige, (1962); Gamborg et al., (1968); Duncan et at., (1985): McCown and Lloyd, (1981); Nitsch and Nitsch, (1969); and Schenk and Hildebrandt, (1972), or derivations of these media supplemented accordingly. Those of skill in the art are aware that media and media supplements such as nutrients and growth regulators for use in transformation and regeneration are usually optimized for the particular target crop or variety of interest. Reagents are commercially available and can be purchased from a number of suppliers (see, for example Sigma Chemical Co., St. Louis, Mo. and Phytotechnology Laboratories, Shawnee Mission, Kans.).

Co-culture and subsequent steps may be performed in dark conditions, or in lighted Percival incubators, for instance for 2 to 5 days with a photoperiod of 16 hours of light, 8 hours of dark. In one embodiment, the light intensity may be, for example, at least about 5 µE, including, at least about 10 µE or 25 µE, including between about 5 uE and about 200 uE or other lighting conditions that allow for normal plastid development at a temperature of approximately 23 to 25° C., and may be performed at up to about 35° C.

EXAMPLES

Those of skill in the art will appreciate the many advantages of the methods and compositions provided by the present invention. The following examples are included to demonstrate the preferred embodiments of the invention. It should be appreciated by those of skill in the art that the techniques disclosed in the examples that follow represent techniques discovered by the inventors to function well in the practice of the invention, and thus can he considered to constitute preferred modes for its practice. However, those of skill in the art should, in light of the present disclosure, appreciate that many changes can be made in the specific embodiments that are disclosed and still obtain a like or similar result without departing from the spirit and scope of the invention. All references cited herein are incorporated herein by reference to the extent that they supplement, explain, provide a background for, or teach methodology, techniques, or compositions employed herein.

Example 1

Separation of Explant Material

Seeds were processed manually, or subjected to automated excision in a rice Sheller (e.g. Grainman® Laboratory Paddy Rice Sheller (e.g. Model #64-115-60-WDC; Grain Machinery Manufacturing Corp., Miami, Fla.), or for instance as described in U.S. Patent Publication 20050005321. In order to obtain meristematic explant material, soybean seeds (cv. A3525; Asgrow Seed Company) were processed to separate the embryo, comprising meristematic tissues, from the seed coat and cotyledon(s). The effect of the internal moisture content of the starting seed at the time of excision on explant yield from this process is shown in Table 1.

TABLE 1

Effect of Internal Moisture Content on Explant Yield

| Moisture Content of Soybean Seed | Explant estimate per Kg of seed processed |
|---|---|
| 6.3% | 1626 |
| 8.2% | 939 |
| 11.5% | 87 |

The temperature of the seed prior to preparation of explant material also affected explant yield. Table 2 illustrates that explants can be excised at various temperatures, including −20° C. to room temperature.

TABLE 2

Effect of Seed Storage Temperature on Explant Yield

| Storage temperature | Meristem estimate per Kg of seed processed |
|---|---|
| Room temperature (about 23-26° C.) | 650.4 |
| 4° C. | 286.2 |
| −20° C. | 267.3 |

Example 2

Recovery of Explant Material

Table 3 illustrates the yield of usable explant tissue given differing seed moisture content at the start of the excision procedure. Lower seed moisture (about 6.2%) allowed for greater yield of explant material by weight of seed processed. This is noteworthy, as the internal moisture content of dry soybean seed when freshly harvested from the field is approximately 9 to 14% and is ideally maintained at about 11% for long term (1 to 20 years) storage. The higher moisture content allows the seeds to be handled without breakage and loss of vigor to the embryo. The inventors discovered that dry seed at the higher moisture content were much less brittle than seed dried to lower internal moisture contents (3% to 7%). This discovery allows s seed to be handled and stored at the ideal internal moisture content for vigor (approximately 9 to 12%), yet manipulated for ideal extraction of dry explants (artificial seeds) by drying seeds to approximately 3% to 7% to achieve a brittleness. This brittle state maintains vigor of the embryo, yet allows for a clean split of the seed between the cotyledons, and thus allows both high quality, and high yield.

The optimum moisture content to achieve a brittle state and thus allow high process yield and high transformation quality explant may vary based on soybean genotype and crop type. This example illustrates the methodology necessary to optimize conditions for a given germplasm source or type of plant seeds.

TABLE 3

Yield of usable explant tissue obtained from seeds with different moisture content.

| Seed moisture content (%) | Run size (grams) | Returned embryo yield (grams) | % Crude yield | Total sample weight (mg) | Meristem containing explants by microscopic evaluation (mg) | Damaged explants or debris (mg) | % good explants by weight | Number of good explants per 1000 mg sample | Meristem estimate for total run (count) | Meristem estimate per kg (count) | Seed estimate per kg (count) | % recovery based on theoretical maximum |
|---|---|---|---|---|---|---|---|---|---|---|---|---|
| 12.5 | 4203 | 67.6 | 1.6 | 500 | 170 | 328 | 34 | 68 | 4597 | 1094 | 6050 | 18.1 |
| 12.2 | 200 | 3.98 | 2.0 | 500 | 160 | 340 | 32 | 64 | 255 | 1274 | 6050 | 21.1 |
| 12.2 | 200 | 3.71 | 1.9 | 500 | 225 | 275 | 45 | 90 | 334 | 1670 | 6050 | 27.6 |
| 14.5 | 200 | 3.25 | 1.6 | 500 | 320 | 180 | 64 | 126 | 410 | 2048 | 6050 | 33.8 |
| 14.5 | 200 | 3.28 | 1.6 | 500 | 250 | 250 | 50 | 102 | 335 | 1673 | 6050 | 27.6 |
| 6.2 | 200 | 6.35 | 3.2 | 500 | 200 | 300 | 40 | 80 | 508 | 2540 | 6050 | 42.0 |
| 6.2 | 200 | 6.08 | 3.0 | 500 | 230 | 270 | 46 | 96 | 584 | 2918 | 6050 | 48.2 |

Example 3

Sterilization of Seeds and/or Explant Material

A number of techniques of sterilizing seeds before excision, as well as sterilizing explants after excision from the seeds were tested. Post-excision sterilization of dry explants using chlorine gas in a vacuum desiccation chamber was tested at time intervals ranging from 15 minutes to 16 hours. Contamination control increased with longer exposure to Cl gas, although fungal contamination grew in treatments in which the exposure to Cl gas had surpassed the survivable threshold of the explants.

Ozone gas treatments were also tested. Both whole seed (before excision) and dry explants (after excision) were exposed to $O_3$ gas in a PLEXIGLAS chamber (OSR-8 Ozone Generator; Ozone Solutions, Sioux Center, Iowa) at various time intervals of 1-24 hours. $O_3$ was used at a concentration of 467 ppm. After seed was exposed to ozone, embryonic material was excised and explant viability was measured. Ozonation of soybean seed for 12 hours or less did not impact viability of subsequently isolated explants, but drastically decreased bioburden found in explants. Ozonation of dry excised explants for as little as 1-4 hours decreased explant health (i.e. number of viable embryos).

Additional tests on pre-excision sterilization of whole seed were performed using a bleach solution of 200 ppm active chlorine, followed by an overnight hydration period (~9 hours) in a solution of 50 ppm active chlorine. These seeds were then allowed to dry in a laminar flow hood (typically for 12-48 hours) before being excised mechanically. A modification to the 50% bleach soak protocol was also tested, in which the seeds were first rinsed with a 70% solution of ethanol. The ethanol was immediately drained (total exposure to ethanol was less than 5 seconds), and then the 50% bleach soak was performed by treating seeds 3-15 min in 50% bleach followed by 3 rinses with water and drying the seeds overnight such that the moisture content was less than 8%. UV light may also be employed to sterilize the plant material.

Example 4

Hydration of Seeds and Explant Material

Studies employing new pre-culture hydration/germination strategies were tested. The types of media used for this step included "bean germination medium" (PGM; Media Table 11), soy inoculum medium (INO; Media Table 11), and prepared log-phase Agrobacterium growth cultures (AGRO). The Agrobacterium growth culture was grown overnight in Lysogeny Broth (LB, also commonly referred to as Luria-Bertani Broth) to log phase, and then centrifuged and resuspended to a final optical density at 660 nm of 0.25 to 0.6. The medium used for the dilution is the same as the soy inoculum medium. Plant Preservative Mixture (PPM™, Product #P820; Phytotechnology Laboratories, Shawnee Mission, Kans.) was also tested at a concentration of 2 mg/L (as per manufacturer recommendations on label). Explants were soaked in this solution overnight at 4° C. Other variations were made in the duration of exposure to respective hydration media, the various temperatures during this exposure, and the extent of saturation in the respective media. Exposure times tested ranged from 0 to 24 hours. Temperatures during longer exposure times (those greater than 4 hours) were either room temp (~26° C.), 23° C., or 4° C. Exposure times of 4 hours or less were all tested at room temperature. As an alternative to completely submerging or substantially saturating explants with liquid media during the hydration process, some treatments employed the use of moistened filter paper (enough liquid to wet, but not to saturate). This was done with filter paper moistened with either BGM or Agrobacterium-culture medium. Hydration was performed in a variety of vessels, including but not limited to conical centrifuge tubes, graduated glass bottles, or a PLANTCON tissue culture container (MP Biomedicals, Irvine, Calif.).

This example also demonstrates that hydration can be done in a variety of media containing various types of carbohydrates such as glucose (INO), and sucrose (BGM). Other carbohydrates such as galactose may be useful in hydration medium.

Example 5

Transformation and Cultivation of Soybean Explants

Agrobacterium-mediated transformation followed the hydration step as indicated in Tables 4-9. Soybean meristem explants were transformed with pMON67438 comprising a CP4 EPSPS gene conferring glyphosate tolerance and a GUS reporter gene. Explants that had been hydrated in something other than Agrobacterium culture medium, i.e. soy inoculum medium (INO) or sterile distilled water (SDW), bean germination medium (BGM), or Plant Preservative Mixture, had that liquid removed, and then the explants were rinsed twice with sterile distilled water. Explants were then placed in a PLANTCON (if not already in one). Prepared Agrobacterium culture (as described above) was added to the container (enough to cover all explants within the PLANTCON). Explants that were hydrated in Agrobacterium culture to begin with remained in that culture, and were also transferred to a PLANTCON.

Explants were then subjected to sonication wounding for 20 seconds while in the PLANTCON according to standard procedures (U.S. Pat. No. 7,002,058). Following sonication wounding, explants were transferred to new PLANTCONS containing a cut-to-size piece of filter paper. 2.5 mL to 5 mL of soy inoculum medium was used to moisten the filter paper. Explants were co-cultured at 23° C. for 2-4 days either in dark or light. Following co-culture, explants were placed on the surface of solid woody plant medium (WPM; Table 12), and implanted into solid woody plant medium at approximately the 17$^{th}$ day post-inoculation, for the remainder of the tissue culture experiment phase. Shoots were transferred to Bean Rooting Medium for rooting (BRM; Table 13). Concentrations of various hormones may be manipulated to effect regeneration. For examples, BAP may be used at 0.04 ppm (0.18 µM) in WPM and IAA may be used at about 0.099 ppm (0.565 µM) in BRM. Other plant growth regulators and concentrations have been routinely utilized to facilitate transformation and regeneration, for instance as described in U.S. Pat. No. 6,384,301.

Explants that had been placed within assay well plates for initial hydration were left there for the entire duration of the experiment life span, including sonication and co-culture periods. For these experiments, liquid media was used instead of solid media, and was replaced with fresh media at ~17 days post inoculation. This demonstrates that the explants are amenable to liquid culture as well as solid (gel-based) tissue culture steps.

Example 6

Comparison of Explant Excision, Sterilization, Storage, and Hydration Parameters Subsequent studies tested a variety of parameters involving seed storage, excision, and sterilization methods and conditions; explant storage conditions; and transformation conditions as they impacted the ability of excised meristematic material to initiate shoot formation (SF), whether or not having been transformed, as well as transformation frequency (TF). These parameters, for either or both seed and explant material, included pre- or post-excision sterilization procedures, storage conditions, hydration conditions, and subsequent tissue culture conditions, including in the absence or presence of selection.

In study SAG_709 (Table 4), whole soybean seed were sterilized prior to excision by immersion in a 50% sodium hypochlorite (bleach) solution. Following sterilization, seeds were rinsed and dried to a moisture content of <8%. Following these steps, explants were prepared and recovered as described in examples 1 and 2. Parameters studied included: length of storage prior to transformation of explant material; storage temperature; and hydration media. The results showed that the explants of the present invention can be used to obtain transformed plants under a broad range of storage temperature and a variety of hydration media. The result of DNA testing showed a normal distribution for copy numbers based on the sample size.

In Study SAG_712 (Table 5), soybean seeds were sterilized with Cl gas prior to dry excision. Following sterilization and dry excision, length of storage and hydration conditions were varied. This was compared with wet excision method as described in U.S. Publ. 20050005321 and U.S. Pat. No. 7,002,058 (Trt 7).

In Study SAG_714 (Table 6), seeds were sterilized prior to excision by immersion in a 50% sodium hypochlorite (bleach) solution. Following sterilization, rinsing, drying, and dry excision, explants were stored for one to three days prior to transformation at various temperatures (e.g. −20° C., 4° C., and room temperature), and hydration conditions were also varied. The ability of explants treated in this manner to form shoots (shoot frequency; "SF") or transformed plants (transformation frequency; "TF") was compared with explants that were prepared by a "wet excision" method, for instance as described in U.S. Patent Application Publication 20050005321 and then dried and stored (Trt 7 and Trt 8).

Transformation has also been demonstrated in explants that were recovered from a hydrated or imbibed seed (referred to as "wet excision" in study SAG_714—Table 6, treatments 7 and 8; and also in study SAG_762—Table 8, treatments 1 and 2) but where the explant was appropriately dehydrated. Wet excision methods are described in U.S. Publ. 20050005321 and U.S. Pat. No. 7,002,058. A typical process for preparing explants by this method is as follows:

1) Dry seeds are rinsed with sterile water, or a solution of Sodium hypochlorite (ranging from 0 ppm to ~30,000 ppm active chlorine, including 50 ppm and 200 ppm active chlorine) for 3 to 20 minutes. Liquid is then drained.

2) Approximately 2 hours later, rehydration medium is applied for 5 to 24 hours. This rehydration medium can be BGM, sterile deionized water, sterile or clean tap water, or a dilute disinfectant solution, such as sodium hypochlorite with an active chlorine content of 50 to 1000 ppm.

3) Following rehydration medium, the seeds may be immediately excised to isolate embryo explants (either by mechanical or manual methods), or may be further rinsed with water or other dilute disinfectant, such as sodium hypochlorite with an active chlorine content of 50 to 1000 ppm for 15 minutes.

4) Following its excision and recovery, the explant is dried and prepared for storage by being spread out in a shallow tray under a flow of air. This is typically done in a clean-air tissue culture hood. Explants were typically allowed to dry for ~18 to 24 hours.

5) Dried explants were stored (typically in sealed 50 mL conical tubes). Storage duration prior to transformation initiation can range from minutes to weeks or months. Temperature conditions during storage can range from room temperature to 80 degrees C.

6) Following desired storage, explants were hydrated for transformation as described in example 4.

Study 716 (Table 7) tested the effect of a 7 day storage period following dry excision on the ability of explants to form shoots.

Study 762 (Table 8) tested the effect of a 7 week storage period on the ability of excised explant material to form shoots. A dry excised embryo that was stored for up to 7 weeks was able to produce a transgenic plant.

An overall summary of shoot-formation and transformation frequencies for the above listed studies is found in Table 9. The results indicate that dry excised as well as wet-excised (and then dried) soybean explants remain viable, retain the ability to form shoots and plants, and may be successfully transformed with heterologous DNA, even after dry storage of excised embryos for periods of time up to 8 weeks under a variety of temperature conditions and types of hydration media. Shoot formation frequency (SF) and transformation frequency (TF) of dry excised and stored explants or wet excised, dried, and stored explants compared favorably with those of explants that were not stored, according to previously described methods (U.S. Publ. 20050005321). The copy number and presence of introduced transgenes (e.g. CP4), and presence of vector backbone sequences (e.g. oriV) was also tested by Southern analysis or by INVADER assay (e.g. Mein et al., 2001) at the R0 generation (Tables 5-9). DNA analysis of R1 plants yielded the same results demonstrating stable and heritable transformation

TABLE 4

| | | | | | SAG709 | | | | | | |
|---|---|---|---|---|---|---|---|---|---|---|---|
| | Trt 1 | Trt 2 | Trt 3 | Trt 4 | Trt 5 | Trt 6 | Trt 7 | Trt 8 | Trt 9 | Trt 10 | Trt 11 |
| Sterilization conditions | Pre-excision sterilization in 50% bleach | | | | | | | | | | |
| Storage conditions | 2 days @ Room Temp | 2 days @ Room Temp | 2 days @ Room Temp | 2 days @ 4° C. | 2 days @ 4° C. | 1 day @ 4° C. | 1 day @ 4° C. | 1 day @ 4° C. | 2 days @ −20° C. | 2 day @ −20° C. | 2 day @ −20° C. |
| Hydration conditions | 4 hours in 15 mL conical tubes; 5 mLs INO | 4 hours in 15 mL conical tubes; 5 mLs agro | 4 hours in 15 mL conical tubes; 5 mLs SDW | 4 hours in 15 mL conical tubes; 5 mLs INO | 4 hours in 15 mL conical tubes; 5 mLs agro | 4 hours in 15 mL conical tubes; 5 mLs SDW | 4 hours in 15 mL conical tubes; 5 mLs INO | 4 hours in 15 mL conical tubes; 5 mLs agro | 4 hours in 15 mL conical tubes; 5 mLs INO | 4 hours in 15 mL conical tubes; 5 mLs agro | 4 hours in 15 mL conical tubes; 5 mLs SDW |
| Explants used | 35 | 34 | 39 | 36 | 56 | 53 | 52 | 96 | 42 | 39 | 30 |
| Shoots obtained | 3 | 0 | 7 | 7 | 13 | 5 | 10 | 9 | 9 | 6 | 4 |
| SF | 8.57% | 0.00% | 17.95% | 19.44% | 23.21% | 9.43% | 19.23% | 9.38% | 21.43% | 15.38% | 13.33% |
| Rooted shoots obtained | 1 | 0 | 0 | 3 | 2 | 1 | 1 | 2 | 3 | 2 | 1 |
| GUS positive root assay | 1 | 0 | 0 | 3 | 2 | 1 | 1 | 1 | 3 | 1 | 1 |
| TF | 2.86% | n/a | n/a | 8.33% | 3.57% | 1.89% | 1.92% | 2.08% | 7.14% | 5.13% | 3.33% |
| DNA test Results for copy number (CriV − or +) | | | | | | | | | | | |
| Negative | 0 | 0 | 0 | 0 | | | NA | | | | |
| 1 Copy | 0 | 0 | 0 | 2 (−) | | | NA | | 1 (−) | 1 (−) | |
| 2 Copy | 0 | 0 | 0 | 1(−) | 1 | | NA | 1 (−) | | 1(−) | |
| 3 Copy | 0 | 0 | 0 | 0 | | | NA | | 1 | 2 | 1 (−) |
| >/= 4 Copy | 1 (−) | 0 | 0 | 0 | 1 (+) | 1 (−) | NA | | | | |

Treatment Averages

| | Average | | DNA Test (GAMA) Results | | | |
|---|---|---|---|---|---|---|
| Treatment | SF | TF | Negative | 1-2 copy | 3-4 copy | >4 copy |
| Room Temperature | 8.84% | 0.95% | 0 | 0 | 0 | 100% |
| 4 degrees | 16.14% | 3.56% | 0 | 69% | 13% | 18% |
| −20 degrees | 16.72% | 5.20% | 0 | 33% | 67% | 0 |
| 2 day storage | 14.92% | 3.80% | 0 | 56% | 44% | 0 |
| 1 day storage | 12.68% | 1.96% | 0 | 67% | 33% | 0 |
| hydration in Agro | 11.99% | 2.70% | 0 | 40% | 20% | 40% |
| hydration in INO | 17.17% | 5.06% | 0 | 57% | 29% | 14.0% |
| hydration in SDW | 13.57% | 1.74% | 0 | 0 | 100% | 0 |

TABLE 5

| | | | | SAG_712 | | | |
|---|---|---|---|---|---|---|---|
| | Trt 1 | Trt 2 | Trt 3 | Trt 4 | Trt 5 | Trt 6 | Trt 7 |
| Sterilization conditions | Pre-excision sterilization in Cl gas | | | | | | |
| Storage conditions | 2 days @ 4° C. | 2 days @ 4° C. | 2 days @ 4° C. | 1 day @ 4° C. | 1 day @ 4° C. | 1 day @ 4° C. | Conventional (e.g. US 2003/0110532) |
| Hydration conditions | 4 hours in 15 mL conical tubes; 5 mLs INO | 4 hours in 15 mL conical tubes; 5 mLs agro | 4 hours in 15 mL conical tubes; 5 mLs SDW | 4 hours in 15 mL conical tubes; 5 mLs INO | 4 hours in 15 mL conical tubes; 5 mLs Agro | 4 hours in 15 mL conical tubes; 5 mLs SDW | Conventional (e.g., US 2003/0110532) |
| # of explants/study | 54 | 58 | 47 | 92 | 90 | 91 | 100 |
| Number of shoots obtained | 3 | 4 | 1 | 16 | 8 | 9 | 8 |
| SF | 5.56% | 6.90% | 2.13% | 17.39% | 8.89% | 9.89% | 8.00% |

TABLE 5-continued

| | | | | | | | |
|---|---|---|---|---|---|---|---|
| Number of rooted shoots obtained | 0 | 0 | 0 | 3 | 2 | 3 | 3 |
| GUS positive root assay | | | | 3 | 2 | 2 | 3 |
| TF | n/a | n/a | n/a | 3.26% | 2.22% | 3.30% | 3.00% |

DNA test Results for copy number (OriV − or +)

| | | | | | | | |
|---|---|---|---|---|---|---|---|
| Negative | 0 | 0 | 0 | 0 | | 0 | |
| 1 Copy | 0 | 0 | 0 | 1 (−) | 2 (−) | 2 (−) | 1 (−) |
| 2 Copy | 0 | 0 | 0 | 1 (−) | | 0 | |
| 3 Copy | 0 | 0 | 0 | 0 | | 1 (−) | 1 |
| >/= 4 Copy | 0 | 0 | 0 | 0 | | 0 | |

Treatment Averages

| | Average | | DNA Test (GAMA) Results | | | |
|---|---|---|---|---|---|---|
| Treatments | SF | TF | Negative | 1-2 copy | 3-4 copy | >4 copy |
| 4 degrees | 8.46% | 1.46% | 0 | 83% | 17% | 0% |
| 2 day storage | 4.86% | n/a | 0 | 0 | 0 | 0 |
| 1 day storage | 12.06% | 2.93% | 0 | 83% | 17% | 0 |
| hydration in Agro | 7.89% | 1.11% | 0 | 100% | 0 | 0 |
| hydration in INO | 11.47% | 1.63% | 0 | 100% | 0 | 0 |
| hydration in SDW | 6.01% | 1.65% | 0 | 67% | 33% | 0 |

TABLE 6

SAG_714

| | Trt 1 | Trt 2 | Trt 3 | Trt 4 | Trt 5 | Trt 6 | Trt 7 | Trt 8 |
|---|---|---|---|---|---|---|---|---|
| Storage conditions | 3 days @ 4° C. | 3 days @ 4° C. | 3 days @ 4° C. | 1 day @ RT | 1 day @ 4° C. | 2 days @ −20° C. | Wet auto excision, then dried; store 1 day @−20° C. | Wet auto excision, then dried; store 1 day @ 4° C. |
| Hydration conditions | 4 hours in 15 mL conical tubes; 5 mLs INO | 4 hours in 15 mL conical tubes; 5mLs agro | 4 hours in 15 mL conical tubes; 5 mLs SDW | 4 hours in 15 mL conical tubes; 5 mLs Agro | 4 hours in 15 mL conical tubes; 5 mLs SDW | 4 hours in 50 mL conical tube; 5mLs Agro | 4 hours in 50 mL tube; 5 mLs Agro | 4 hours in 50 mL tube; 5 mLs Agro |
| Sterilization method | Pre-excision 50% bleach | | | | | Post-excision Cl gas | Standard protocol | Standard Protocol |
| # of explants/study | 98 | 89 | 72 | 62 | 50 | 86 | 34 | 44 |
| Number of shoots obtained | 8 | 13 | 4 | 6 | 6 | 0 | 7 | 9 |
| SF | 8.16% | 14.61% | 5.56% | 9.68% | 12.00% | 0.00% | 20.59% | 20.45% |
| Number of rooted shoots obtained | 2 | 3 | 0 | 1 | 2 | 0 | 2 | 1 |
| GUS Positive Root assay | 2 | 2 | | 1 | 2 | | 2 | 1 |
| TF | 2.04% | 3.37% | n/a | 1.61% | 4.00% | n/a | 5.88% | 2.27% |

DNA test Results for copy number (OriV − or +)

| | | | | | | | | |
|---|---|---|---|---|---|---|---|---|
| Negative | | | | | | | | |
| 1 Copy | | | 1 | | | | | |
| 2 Copy | | | | | | 1 | 2 | 1 |
| 3 Copy | 1 | | 1 | | | | | |
| >/= 4 Copy | | | | | | | | |

TABLE 6-continued

Treatment Averages

| Treatments | Average | | DNA Test (GAMA) Results | | | |
|---|---|---|---|---|---|---|
| | SF | TF | Negative | 1-2 copy | 3-4 copy | >4 copy |
| 4 degrees | 10.08% | 2.35% | 0 | 50% | 50% | 0 |
| Room Temp | 9.68% | 1.61% | 0 | 0 | 0 | 0 |
| 1 day storage | 10.84% | 2.81% | 0 | 100% | 0 | 0 |
| 3 day storage | 9.44% | 1.80% | 0 | 33% | 67% | 0 |
| hydration in Agro | 12.14% | 2.49% | 0 | 67% | 33% | 0 |
| hydration in INO | 8.16% | 2.04% | 0 | 50% | 50% | 0 |
| hydration in SDW | 8.78% | 2.00% | 0 | 100% | 0 | 0 |
| Wet excised, then dried | 20.52% | 4.08% | 0 | 100% | 0 | 0 |

TABLE 7

SAG_716

| | Trt 1 | Trt 2 | Trt 3 |
|---|---|---|---|
| Storage conditions: | 7 days @ 4° C. | 7 days @ 4° C. | 7 days @ 4° C. |
| Hydration conditions | 4 hours in 50 mL conical tubes; 5 mLs Agro | 4 hours in 50 mL conical tubes; 5 mLs INO | 4 hours in 50 mL conical tubes; 5 mLs SDW |
| Sterilization method | Pre-excision 50% bleach | | |
| # of explants/study | 104 | 122 | 96 |
| Number of shoots | 3 | 1 | 2 |
| SF | 2.88% | 0.82% | 2.08% |
| Number of rooted shoots | 0 | 0 | 0 |
| TREATMENT AVERAGES: | | | |
| | SF | | |
| Hydration in Agro | 2.88% | | |
| Hydration in INO | 0.82% | | |
| Hydration SDW | 2.08% | | |
| Avg. all trts at 7 day storage | 1.93% | | |

TABLE 8

SAG_762

| | Trt 1 | Trt 2 | Trt 3 | Trt 4 |
|---|---|---|---|---|
| Storage conditions: | Wet auto excision, then dried; stored ~7 wks @ 4° C. | Wet auto excision, then dried; stored ~7 wks @ −20 C. | Dry excised, stored ~8 wks @ 4° C. | Dry excised, stored ~7 wks @ 4° C. |
| Hydration conditions | 4 hours in 150 mL pyrex beaker; 50 mLs INO | 4 hours in 150 mL pyrex beaker; 50 mLs INO | 4 hours in 50 mL conical tubes; 25 mLs INO | 4 hours in 50 mL conical tubes; 25 mLs INO |
| Sterilization method | Pre-germination as per SOP | | Pre-excision 50% bleach | |
| # of explants/study | 425 | 650 | 275 | 321 |
| Number of shoots | 2 | 12 | 6 | 5 |
| SF | 0.47% | 1.85% | 2.18% | 1.56% |
| Number of rooted shoots | 0 | 0 | 0 | 1 |
| GUS root assay | | | | 1 |
| TF | n/a | n/a | n/a | 0.31% |

TABLE 9

Summary of shoot-formation and transformation frequencies obtained.

| Treatment Averages | Average | | DNA Test (GAMA) Results | | | |
|---|---|---|---|---|---|---|
| Treatments | SF | TF | Negative | 1-2 copy | 3-4 copy | >4 copy |
| Room Temp | 9.26% | 1.28% | 0.00% | 0.00% | 0.00% | 100.00% |
| 4 degrees | 11.56% | 2.46% | 0.00% | 67.33% | 26.67% | 6.00% |
| −20 degrees | 16.72% | 5.20% | 0.00% | 57.00% | 42.00% | 0.00% |
| 1 day storage | 11.86% | 2.57% | 0.00% | 83.33% | 16.67% | 0.00% |
| 2 day storage | 9.89% | 1.90% | 0.00% | 56.00% | 44.00% | 0.00% |
| 3 day storage | 9.44% | 1.80% | 0.00% | 33.00% | 67.00% | 0.00% |
| More than 7 wk storage | 1.51% | 0.08% | 0.00% | 100.00 | 0.00% | 0.00% |
| hydration in INO | 9.41% | 2.18% | 0.00% | 78.50% | 14.50% | 7.00% |
| hydration in Agro | 8.73% | 1.57% | 0.00% | 69.00% | 15.67% | 4.67% |
| hydration in SDW | 7.61% | 1.35% | 0.00% | 55.67% | 44.33% | 0.00% |
| Wet excised & dried | 10.84% | 2.04% | 0.00% | 100.00% | 0.00% | 0.00% |
| Dry excised | 9.64% | 2.03% | 0.00% | 59.69% | 25.58% | 14.71% |

Another parameter that was varied in *Agrobacterium*-mediated transformation was a change in the timing of *Agrobacterium* culture onset, and sonication wounding initiation. Instead of waiting for 1 hour or more for dry explants to hydrate, sonication wounding procedures in some studies were initiated immediately upon submersion in the hydration medium. Alternatively, some treatments received a 1 to 2 day delay in the onset of *Agrobacterium* culture inoculation. Instead of being inoculated immediately after the hydration step, these explants were placed on moistened filter paper for the delay period, and then inoculated and sonication procedures were completed. In a different treatment, the sonication wounding step was left from the procedure completely, as explants were being hydrated on filter paper moistened with *Agrobacterium* culture.

Also tested was a delayed onset of selection pressure (e.g. exposure to glyphosate). Instead of transferring explants onto solid media with selection compound at 2-4 days post inoculation studies received liquid WPM without glyphosate for additional 48 hours, or 1 week before being transferred to the solid WPM with selection compound to terminate or at least retard the growth of non-transformed cells.

An alternative to *Agrobacterium*-mediated transformation was also tested. Dry excised explants were inoculated with *Rhizobium leguminosarum* strains RL 2370LBA & RL 2048G, pMON96033. The protocol for *Rhizobium*-mediated transformation was similar to *Agrobacterium*-mediated transformation, except for replacing the bacterial strain with *Rhizobium*.

A cytokinin, 6-Benzylamino purine (BAP) was also tested as an additive to the *Agrobacterium* culture inoculum medium (also referred to as soy inoculum medium, INO) (e.g. McCabe and Martinell, 1993).

Example 7

Preparation and Transformation of Cotton Explants

Excised cotton (cv STN 474) meristem explants dried after excision and stored dried for 30 days or more are viable after re-hydration and co-culture transformation with *Agrobacterium*. The protocol for cotton meristem transformation essentially followed the method of McCabe and Martinell (1993). Seeds were excised and prepared as per McCabe & Martinell (1993), with the exception that excised embryos were spread out and left in an open container until dry. Storage conditions, and seed pre-sterilization, re-hydration, *Agrobacterium* inoculation, co-culture and tissue culture procedures were essentially identical to those described for soy. Consistent with results from soybean, shoots and young leaves were observed on cultured cotton explants following transformation of meristematic tissue with exogenous DNA.

Example 8

Media Used

TABLE 10

BEAN GERMINATION MEDIA (BGM)

| COMPOUND: | QUANTITY PER LITER |
|---|---|
| BT STOCK #1 | 10 mL |
| BT STOCK #2 | 10 mL |
| BT STOCK #3 | 3 mL |
| BT STOCK #4 | 3 mL |
| BT STOCK #5 | 1 mL |
| SUCROSE | 25 g |
| Adjust to pH 5.8. | |
| ADDITIONS PRIOR TO USE: | PER 1 L |
| CEFOTAXIME (50 mg/mL) | 2.5 mL |
| FUNGICIDE STOCK | 3 mL |
| BT Stock for Bean Germination Medium | |
| Bt Stock 1 (1 liter) | |
| $KNO_3$ | 50.5 g |
| $NH_4NO_3$ | 24.0 g |
| $MgSO_4 \cdot 7H_2O$ | 49.3 g |
| $KH_2PO_4$ | 2.7 g |
| Bt Stock 2 (1 liter) | |
| $CaCl_2 \cdot 2H_2O$ | 17.6 g |
| Bt Stock 3 (1 liter) | |
| $H_3BO_3$ | 0.62 g |
| $MnSO_4 H_2O$ | 1.69 g |
| $ZnSO_4 7H_2O$ | 0.86 g |
| KI | 0.083 g |
| $NaMoO_4 \cdot 2H_2O$ | 0.072 g |
| $CuSO_4 \cdot 5H_2O$ | 0.25 mL of 1.0 mg/mL stock |
| $CoCl_4 \cdot 6H_2O$ | 0.25 mL of 1.0 mg/mL stock |
| Bt Stock 4 (1 liter) | |
| $Na_2EDTA$ | 1.116 g |
| $FeSO_4 \cdot 7H2O$ | 0.834 g |
| Bt Stock 5 (500 mL) | |
| Thiamine-HC1 | 0.67 g |
| Nicotine Acid | 0.25 g |
| Pyridoxine-HCl | 0.41 g |

TABLE 10-continued

BEAN GERMINATION MEDIA (BGM)

| COMPOUND: | QUANTITY PER LITER |
|---|---|
| Fungicide Stock (100 mL) | |
| Chlorothalonil (Bravo) 75% WP | 1.0 g |
| Captan 50% WP | 1.0 g |
| Add sterile distilled water to 100 mL | |

TABLE 11

SOY INOCULUM MEDIUM (INO)

| | amount per liter |
|---|---|
| Stock #1 (Majors) | 1 mL |
| B5 Stock #2 (Calcium Chloride) | 1 mL |
| B5 Stock #3 (Minors) | 1 mL |
| B5 Stock #5 (Iron) | 1 mL |
| Potassium Nitrate ($KNO_3$) | 1 g |
| Glucose | 30 g |
| MES | 3.9 g |
| Add water to 1 L | |
| Initial pH: Adjusted to 5.4 with KOH | |
| Autoclave | |
| B5 Stock #4 (Vitamins) (F.S.) | 1 mL |
| Store at Room temp. | |

| B5 STOCK #1 | Amount per liter: |
|---|---|
| TC Water | 750 mL |
| Magnesium Sulfate | 100 g |
| Ammonium Sulfate | 53.6 g |
| Sodium Phosphate Monobasic Anhydrous | 60 g |
| Stir until completely dissolved | |
| Bring to 1 L with TC water | |

| | Amount per liter |
|---|---|
| B5 STOCK #2 | |
| TC Water | 750 mL |
| Calcium Chloride | 60 g |
| Stir until completely dissolved | |
| Bring to 1 L with TC water | |
| B5 STOCK #3 | |
| TC Water | 750 mL |
| Boric Acid | 0.3 g |
| Manganese Sulfate | 1 g |
| Zinc Sulfate Heptahydrate | 0.2 g |
| Potassium Iodide | 0.075 g |
| Sodium Molybdate Dihydrate | 0.025 g |
| Cupric Sulfate (1 mg/mL) | 2.5 mL |
| Cobalt Chloride (1 mg/mL) | 2.5 mL |
| Stir until completely dissolved | |
| Bring to 1 L with TC Water | |
| B5 STOCK #4 | |
| TC Water | 750 mL |
| Myo-Inositol | 10 g |
| Nicotinic Acid | 0.1 g |
| Pyridoxine HCl | 0.1 g |
| Thiamine HCl | 1 g |
| Stir until completely dissolved | |
| Bring to 1 L with TC Water | |
| B5 STOCK #5 | |
| TC Water | 750 mL |
| Sequestrene | 2.8 g |
| Stir until completely dissolved | |
| Bring to 1 L with TC Water | |

TABLE 12

WOODY PLANT MEDIUM (WPM)
with 75 uM glyphosate as a selection agent

| COMPOUND: | Amount per liter |
|---|---|
| WPM salt (Phytochem) | 2.41 g |
| Sucrose | 20.0 g |
| Calcium Gluconate (Sigma) | 1.29 g |
| Clearys Fungicide (Carlin) | 0.03 g |
| pH | 5.6 |
| AgarGel (Sigma) | 4.0 g |
| Autoclave | |
| Carbenicillin (40 mg/ml) | 5.0 ml |
| Ticarcillin (100 mg/ml) | 1.0 ml |
| Cefotaxime (50 mg/ml) | 4.0 ml |
| Glyphosate (0.5M FS Stock) | 0.15 ml |

TABLE 13

BRM (BEAN ROOTING MEDIA) (for 4 L)

| | |
|---|---|
| MS Salts | 8.6 g |
| Myo-Inositol | 0.40 g |
| Bean Rooting Media Vitamin Stock | 8 mL |
| L-Cysteine (10 mg/mL) | 40 mL |
| Sucrose (Ultra Pure) | 120 g |
| pH 5.8 | |
| Washed Agar | 32 g |
| ADDITIONS AFTER AUTOCLAVING: | |
| BRM Hormone Stock | 20.0 mL |
| Ticarcillin/clavulanic acid | 4.0 mL |
| (100 mg/mL Ticarcillin) | |
| BEAN ROOTING MEDIA VITAMIN STOCK(1 liter) | |
| Glycine | 1.0 g |
| Nicotinic Acid | 0.25 g |
| Pyridoxine HCl | 0.25 g |
| Thiamine HCl | 0.05 g |
| BRM Hormone Stock (Amount for 1 liter) | |
| | 6.0 mL IAA (0.033 mg/mL) |
| | 4.0 mL SDW |

Example 9

High Throughput Single Seed Excision

Figure 2:
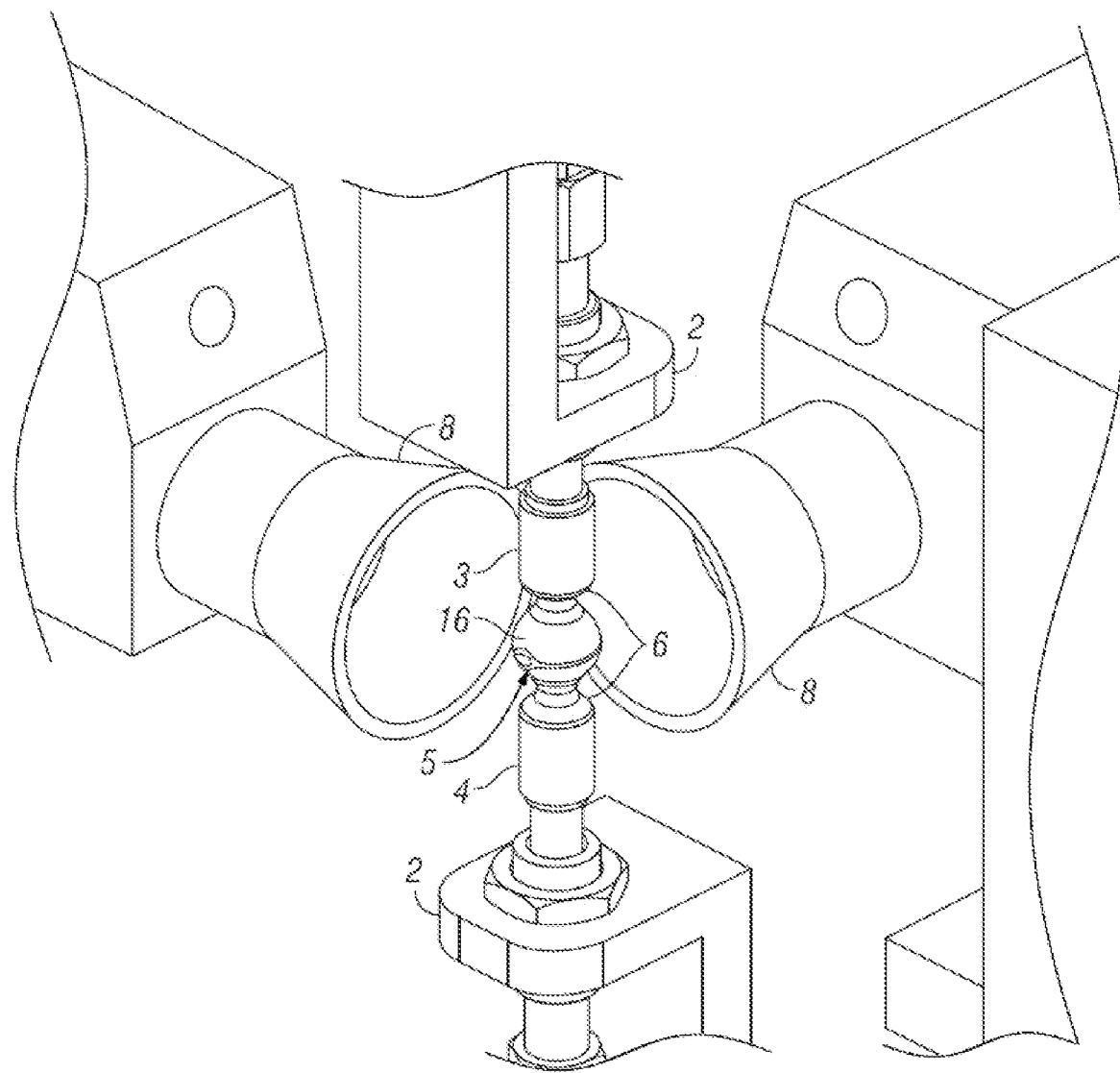
FIG. 2: Partial perspective view of apparatus (FIG. 3) for high throughput explant excision from single seed using vacuum cups.
Figure 3:
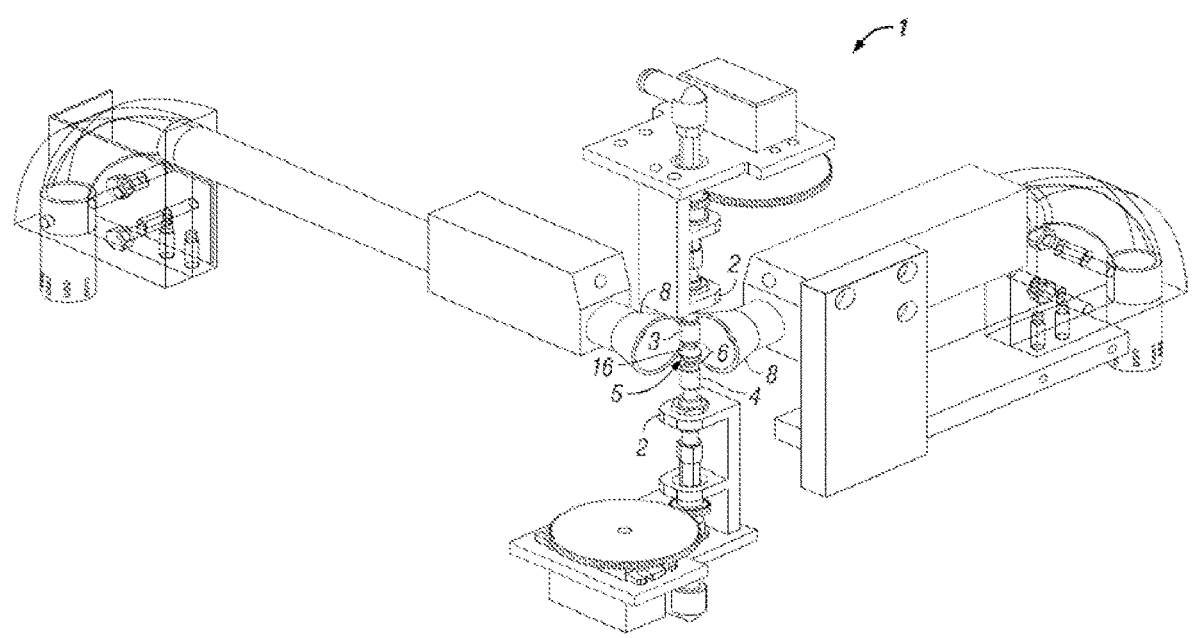
FIG. 3: Simplified representation of an apparatus with vacuum cups for the excision of explant material from singulated seed.

The dry excision process may also be accomplished by use of a singulation system to provide individual (singulated) seeds for processing. After singulation the seed (e.g. a soybean seed) is manipulated by a vacuum cup system to locate the seed. The seed is then placed between a set of vacuum cups and the seed is pinched between the cups, allowing removal of the seed coat by use of a blast of high pressure air alternatively a similar arrangement to pulse, sandblast, or air blast the seed coat from the seed. As shown in FIGS. 2-3, the seed (16) is placed on the lower vacuum cup (6) and the seed is pinched by lowering an upper vacuum cup (6). The seed and the two vacuum cups are then rotated in opposite directions to produce a shearing force point or plane (5) along the center of the elliptical axis of the seed to facilitate the splitting of the seed in the elliptical axis plane. Upon splitting the upper vacuum cup is lifted, and/or one of the vacuum generators (8) is turned on, allowing manipulation of the explant and its separation from other portions of the seed. The explant may then be moved to a desired location such as a tube or a well plate. In FIGS. 4-5 a similar concept is executed, with the inclusion of a metal serrated surface to help to rotate the seed without slipping.

This system includes vacuum placement and pickup units. Although the explant may comprise some cotyledonary tissue in addition to its embryonic tissue, it contains at least some of the meristematic region of the embryo such that typically the explant can produce a shoot within 12 weeks of the onset of tissue culture growth conditions.

The object of this process is to remove the meristematic tissue of the seed under dry conditions on a single seed high-speed basis and to then place the explant in a suitable container for additional transformation steps. Additional explant processing (e.g. sterilization, culling or hydration) may also be performed between the removal of the explant from the seed and its delivery to the container. Additional processing could also include advance imaging of the explant for desirable traits and characteristics, sterilization and transformation treatments. Alternatively, seed could be imaged and sorted for viability and suitability before going through the singulating and explant removal process. Such methods allowing for high throughput explant excision can be made more efficient through parallel systems.

FIGS. 2-5 and 7-9 illustrate embodiments of mechanical separators and cleaner/sterilizers for use in excising transformable embryonic tissue from seed. FIGS. 2-5 illustrate mechanisms for holding a single seed as a shear force is applied, FIGS. 7-9 illustrate embodiments for mechanically cleaning and sanitizing explant material using, for example, an ion generator, charged plates to collect mold, dust, etc.; or UV germicidal lamps.

Referring now to FIGS. 2-5, which generally illustrate examples of a mechanized apparatus for excising embryonic tissue from singulated seed (16), the singulated seed is held so as to apply a shear force as described. In FIGS. 2-5, the first and second vacuum cups (6) and first and second knurled posts (7) turn in opposite directions as a single seed rests or is pinched against them, resulting in fracture of the singulated seed. Other means for holding singulated seed, such as rollers or grates that allow application of an appropriate shear force, may also be employed.

Upon fracturing of the seed and excision of transformable embryonic tissue, the explant comprising embryonic tissues (e.g. FIG. 1) may be moved to a desired location or container for immediate use or storage under appropriate conditions, for instance as described in Example 6 above. This method for excising explant material from singulated seed allows automated high throughput preparation of convenient amounts of transformable embryonic tissues.

Cleaning, culling, sterilization, and selection procedures may be applied to non-excised seed in bulk, or following singulation, or they may be applied to explant material following excision. FIGS. 7-9 illustrate exemplary cleaner/sanitizers for performing such operations on explant material.

Example 10

Stacked Equipment for High-Throughput Explant Preparation

As shown in FIG. 10, the seeds are placed in the mechanized apparatus on top (e.g. a Grainman® speller; see Example 1) to be split as also described, for example, in Example 9 and in FIG. 6. Much of the light material, such as seed coats, are separated by aspiration during the excision process, and the heavier seed fractions, such as cotyledon pieces and explants fall through for further separation of cotyledons from other explant material. In this "stacked" configuration (FIGS. 10-11), the heavier fraction now falls directly into an automatic separator which separates the cotyledons from the explants, for instance by size exclusion with vibrating mesh screens and gravity (e.g. as achieved by the CLIPPER OFFICE TESTER or similar component). Airflow may also be used to aspirate dust and other light seed debris away from the desired material, to clean and/or to sterilize the material (e.g. FIGS. 7-9; FIG. 11). These machines and processes are also described individually (e.g. Example 9), however their combination by stacking for continuous flow-through represents a further improvement in the process and apparatus.

Example 11

Transformation of Dry-Excised Soy Explants Stored for Extended Periods of Time

Dry-excised explants were stored for up to 20 months at −20'C to 4° C., and then tested for survival, transformability and vigor. Explant survival and overall vigor appeared to he similar in all treatment groups, regardless of storage conditions or temperature compared to control treatment (Treatment 1). This demonstrates the ability to store dry-excised explants for almost two years without detriment. Explants from each treatment were tested for transient GUS expression 4 days after inoculation. Table 14 shows a comparison of meristem specific gus expression between treatments, scored on a scale from 0-9, with 0 being no visible expression, and 9 being extensive expression in all 3 meristems of the embryo. This demonstrates that dry-excised explants can not only survive long-term storage in various conditions without significant loss of vigor, but they also retain amenability to transformation. Thus it is now possible to excise large quantities of explants during off-peak times for later use, which represents significant potential cost savings and flexibility in planning and executing transformation studies.

TABLE 14

Effect of storage duration and temperature on explant transformation.

| Treatment | Seed Sterilization Technique | Excision technique | Storage duration | Storage temperature | Transient gus expression (scale of 0-9) |
|---|---|---|---|---|---|
| 1 & 2 | 50% bleach rinse | Automated dry excision with Grainman Rice dehuller | None | NA | 0.90, 1.60 |
| 3 | 50% bleach rinse | Automated dry excision with Grainman Rice dehuller | 17 months | 4° C. | 0.20 |
| 4 | 50% bleach rinse | Automated dry excision with Grainman Rice dehuller | 17 months | −20° C. | 0.10 |
| 5 | 50% bleach rinse | Manual dry excision | 20 months | 4° C. | 0.70 |
| 6 | 50% bleach rinse | Manual dry excision | 20 months | −20° C. | 1.50 |

Example 12

Identification of Suitable Pre-Inoculation Culture ("Pre-Culture") Compositions and Conditions It is likely that dry excised explants are still in a state of semi-dormancy when they are inoculated with *Agrobacterium* for transformation. Thus a method was developed to stimulate the metabolic activity of the dry excised explants prior to *Agrobacterium* inoculation, for increasing their transformation competency. That is, by manipulating the biology of the dry explant, it is possible to increase % germline positive events per explant by 2 to 10 fold.

Several media compositions: BGM (Table 10), INO (Table 11), or OR (Table 15) were tested at 23° C. and/or 28° C. temperatures, and under different light/dark conditions from 1 to 5 days, for their ability to enhance transformation competency. After pre-culturing step, explants were pooled together and inoculated with the *Agrobacterium* culture according to the method described in Example 5. Transient GUS expression assays performed on explants showed increased GUS activity in the pre-cultured treatments after 2 days and 4 days of co-culture.

Plant losses occurred due to fungal infection in some of the pre-culturing experiments, but overall TF of the dry excised explants that were pre-cultured on filter papers wetted with BGM at 23° C. in dark for 5 days appeared to be highest when compared with dry excised explants that were not pre-cultured. The losses due to fungal contamination could be mitigated by using an anti-fungal agent such as BRAVO 75 and Captan 50 at about 1% each during the pre-culture and/or co-culture step. Southern blot and INVADER analysis of the plants produced in this example with a CP4 probe confirmed the transgenic nature of these plants.

TABLE 15

| SOY Organogenic (OR) MEDIUM | |
|---|---|
| COMPOUND: | PER 4 LITER: |
| MS Salts | 17.2 g |
| 3X Minor MS Salts | 40 ml |
| Nicotinic Acid (1 mg/ml) | 4 ml |
| Pyridoxine HCl (1 mg/ml) | 4 ml |
| Thiamine HCl (1 mg/ml) | 46.8 ml |
| Sucrose (Ultra Pure) | 120 g |
| Myo-Inositol (Cell Culture Grade) | .40 g |
|  | pH 5.8 |
| Washed Agar | 32 g |
| ADDITIONS AFTER AUTOCLAVING: | |
| Proline (2.5 m Stock) | 19.2 ml |
| TSG/OR Hormone Stock | 40.0 ml |

TABLE 16

Effect of pre-culture on dry explant; transformation frequency using pMON10343.

| Explant Type | Pre-culture Media composition and conditions | Explants | Rooted Shoots | TF | % Fungal loss (Plantcons) |
|---|---|---|---|---|---|
| WET | None | 300 | 15 | 5.00% | 0% |
| DRY | None | 650 | 6 | 0.92% | 13% |
| DRY | BGM, 5 d 23° dark | 972 | 29 | 2.98% | 0% |
| DRY | BGM, 5 d 23° C. 16/8 light | 365 | 1 | 0.27% | 44% |
| DRY | BGM, 5 d 28° C. dark | 315 | 3 | 0.95% | 7% |
| DRY | BGM, 5 d 28° C. 16/8 light | 188 | 1 | 0.53% | 62% |

Studies were repeated comparing two constructs, pMON101343, comprising one T-DNA that comprises a CP4 gene specifying glyphosate resistance and an OriV replication origin; and pMON107350 comprising one T-DNA that comprises a CP4 gene specifying glyphosate resistance and an OriR replication origin (e.g., see US20070074314) in the vector backbone. Again, pre-culturing of dry explants boosted TF as compared to the TF of non pre-cultured dry explants, as shown in Table 17.

TABLE 17

Additional studies on pre-culture of dry-excised explants.

| Explant type and vector | # Explants | # Rooted Shoots | TF |
|---|---|---|---|
| pMON101343 | | | |
| WET | 535 | 16 | 2.99% |
| DRY | 1331 | 8 | 0.60% |
| DRY PRECULTURE | 2437 | 43 | 1.76% |
| pMON107350 | | | |
| WET | 671 | 11 | 1.64% |
| DRY | 190 | 0 | 0.00% |
| DRY PRE-CULTURE | 500 | 9 | 1.80% |

As shown in Table 18, pre-cultured dry excised explants also yielded higher TFs when explants were cultured in liquid regeneration medium (media of Table 12 except for AgarGel) which was removed and added automatically using a robotic system. TF appeared to be even higher with the liquid regeneration medium with a pre-culturing step. Wet excised explants in liquid media appear to have had low TF due to contamination.

Pre-culturing surprisingly improves competency for transformation and improves transformation uniformity. Such improvements reduce variability during production runs at industrial scale for producing transgenic soybean plants and are likely to improve TFs where selection agents in general yield lower TFs.

TABLE 18

Pre-culture of dry excised explants; comparison of solid and liquid media.

| Explant type pMON101343 | Pre-culture Media compositions and conditions | Regeneration medium | Explants | Rooted Shoots | TF |
|---|---|---|---|---|---|
| WET | None | solid WPM | 460 | 17 | 3.70% |
| WET | None | liquid WPM | 31 | 0 | 0.00% |
| DRY | None | solid WPM | 1286 | 8 | 0.62% |
| DRY | None | liquid WPM | 128 | 0 | 0.00% |
| DRY | BGM, 5 d 23° C. dark | solid WPM | 1257 | 33 | 2.63% |
| DRY | BGM, 5 d 23° C. dark | liquid WPM | 111 | 3 | 2.70% |

Example 13

Production of Transgenic Soybean Plants Using Dry Soybean Explants and Spectinomycin Selection Dry, viable, seeds (properly stored quality soybean seed comprise approximately 10 to 12% internal moisture content) were rinsed with sterile water, or a solution of Sodium hypochlorite (ranging from 0 ppm to ~30,000 ppm active chlorine, including 50 ppm and 200 ppm active chlorine) for 3 to 20 minutes. Liquid was then drained. This process raises the internal moisture content to approximately 16%. Following this brief surface sanitation step, the seed internal moisture content was lowered in a commercial seed dryer with a flow of dehumidified air (temperature controlled to approximately 60 to 90 degrees F.) to less than 8%.

Following desired storage, explants were hydrated for transformation. The types of media used for this step may be varied and included "bean germination medium" (BGM; Table 10), soy inoculum medium (INO; Table 11), and prepared log-phase *Agrobacterium* growth cultures (AGRO). The *Agrobacterium* growth culture was grown overnight in Lysogeny Broth (LB, also commonly referred to as Luria-Bertani Broth) to log phase, and then centrifuged and resuspended to a final optical density at 660 nm of 0.25 to 0.6. The medium used for the dilution is the same as the soy inoculum medium. Hydration temperatures and durations also can be varied, with some experiments having explants that were soaked in one of these solutions overnight at 4° C. Other variations were made in the duration of exposure to respective hydration media, the various temperatures during this exposure, and the extent of saturation in the respective media. Exposure times tested ranged from 0 to 24 hours, Hydrations during longer exposure times (those greater than 4 hours) were done at either room temp (~26° C.), 23° C., or 4° C. Exposure times of 4 hours or less were all tested at room temperature. As an alternative to completely submerging or substantially saturating explants with liquid media during the hydration process, some treatments employed the use of moistened filter paper (enough liquid to wet, but not to saturate). This was done with filter paper moistened with either BGM or *Agrobacterium*-culture medium. Hydration was performed in a variety of vessels, including but not limited to conical centrifuge tubes, graduated glass bottles, or a PLANTCON tissue culture container (MP Biomedicals, Irvine, Calif.).

After hydration, explants were briefly sonicated in the presence of the appropriate *Agrobacterium* cultures. Co-culture and subsequent steps were performed in lighted Percival incubators for 2 to 5 days (16 hours of light, 8 hours of dark, with light intensity of at least 5 μE to 200 μE) at a temperature of approximately 23 to 25° C., and may be performed up to about 35° C. Light is known to promote gene transfer from *Agrobacterium* to plant cells. Spectinomycin was applied as a selection agent either during hydration, in co-culture steps, and/or following co-culture at 15 mg/L to 1000 mg/L.

Phenotype positive shoots (plants) were routinely recovered, as shown in Table 19, using the construct, pMON96999, comprising one T-DNA comprising an aadA gene and an OriV origin of replication or the construct, or pMON101343 comprising one T-DNA comprising a CP4 gene and an OriV origin of replication. By "phenotype positive" in the presence of to spectinomycin, it is meant that shoots are green and robust, while phenotype negative shoots are weak and bleached (white), if they elongate at all. Spectinomycin or glyphosate were used in the regeneration medium (both solid or liquid) at the concentration shown in Table 19.

TABLE 19

Transformation frequency of dry soybean explants using glyphosate or spectinomycin as selective agent.

| Spectinomycin (% TF) | | | | Glyphosate (% TF) |
|---|---|---|---|---|
| 25 ppm | 50 ppm | 100 ppm | 200 ppm | 50 uM |
| 4.66 | 4.24 | 6.34 | 5.99 | 2.00 |

Spectinomycin was also used as a selective agent for transformation of dry excised soybean embryos utilizing the following conditions: 1 hr hydration in INO medium, 4 days co-culture in INO, 150 ppm spectinomycin, with culture on solid or liquid WPM (Table 12, with or without added agar). Temperatures of 23-25 or 28° C., up to about 35° C., may be utilized. Phenotype positive shoots were harvested at 8 and 10 weeks post *Agrobacterium* inoculation, and rooting was induced on solid BRM (Table 13) with 150 ppm Spectinomycin. Very high transformation frequencies of 25.05% and 19.27% were obtained in two different studies. Explants used in this study were not treated with cytokinin-like plant growth regulators (such as TDZ or BAP), thus demonstrating that high transformation frequency could be achieved in the absence of such plant growth regulators.

Example 14

Production of Transgenic Soybean Plants Using Dry Soybean Embryos, Spectinomycin, and Liquid Culture Medium In these studies, explants were initially hydrated and eventually regenerated on WPM solid media with liquid overlay or WPM liquid medium as above. All explants were transferred at 6 weeks post inoculation to trays containing Oasis® Wedge System (Smithers-Oasis USA; Kent, Ohio) and a simplified liquid medium (0.5 g/L WPM with 0.25 mg/L IBA). Rooted and shooted. $R_0$ plants were obtained two to 4 weeks later. In all studies and treatments, initial hydration of explants was done for 1 hour in the respective media as shown in the Table 20. Liquid culture medium was the same as in Table 12 except glyphosate was replaced by spectinomycin at 150 ppm. In liquid overlay treatment both solid and liquid culture media were used; liquid medium was dispensed over the top of explants as they were lying on solid medium at a specified time during tissue culture as identified in the Table 21. This was done as a type of media refreshment and avoids the need for transferring explants from old media to new media. In the control treatments, explants were surface plated on a solid WPM medium (Table 12). Shoots were harvested and rooted on solid BRM as described above, except glyphosate was replaced with spectinomycin at 150 ppm.

TABLE 20

Transformation frequency with given hydration conditions.

| Treatment | Hydration medium | Incubation with Agrobacteria | TF % (mean of 3 repeats) |
|---|---|---|---|
| 1 - Control | INO | 0 minutes | 3.10% |
| 2 | BGM w/o cefotaxime | 0 minutes | 14.67% |
| 3 | BGM w/o cefotaxime | 15 minutes | 15.45% |
| 4 | BGM w/o cefotaxime | 30 minutes | 18.50% |
| 5 | INO | 0 minutes | 13.98% |
| 6 | INO | 15 minutes | 9.64% |
| 7 | INO | 30 minutes | 13.79% |

TABLE 21

Liquid overlay timing.

| Treatment | Liquid overlay timing | Liquid medium overlay volume on solid WPM | Oasis® Wedge transfer for regeneration | TF % (mean of repeats) |
|---|---|---|---|---|
| Control- 1 | NA | None | No | 8.00% |
| 2 | None | None | Yes | 14.67% |
| 3 | 3 weeks post inoculation | 5 mLs | Yes | 15.45% |
| 4 | 3 weeks post inoculation | 10 mLs | Yes | 18.50% |
| 5 | 4 weeks post inoculation | 5 mLs | Yes | 13.98% |
| 6 | 4 weeks post inoculation | 10 mLs | Yes | 9.64% |

Example 15

Production of Transgenic Soybean Plants Using Dry Soybean Embryos, Spectinomycin, and Transferring the Whole Regenerated Explant with a Pre-Culturing Step In these studies, as with Example 12, a pre-culturing step (5 days 23° C. dark in BGM) was used. A one hour hydration of the dry excised explant on INO medium was also done before the pre-culturing step. About 12 mls of liquid WPM containing 150 ppm of spectinomycin was dispensed directly into the co-culture PLANTCON after the co-culture period, and explants were surface plated on solid WPM containing 150 ppm spectinomycin 4 days later. In this example, phenotype positive green shoots were identified at about week 4 of regeneration and transferred from WPM regeneration medium to trays containing Oasis® Wedge System (Smithers-Oasis USA; Kent, Ohio) and a simplified liquid medium (0.5 g/L WPM with 0.25 mg/L IBA). Rooted and shooted $R_0$ plants were obtained two to 4 weeks later. Overall, pre-culturing in these studies also improved TF % (Table 22). Percentage quality events shown below (Table 22) refers to the proportion of transgenic events demonstrating the presence of 1-2 copies of both a gene of interest (GUS) and a marker gene (aadA) by Invader™ assay. Estimated marker-free TF (mTF) refers the % of events without the marker gene. Explants used in this study were treated with 1.0 ppm TDZ during co-culture, thus demonstrating that high transformation frequency with dry explants could be achieved in the presence of a cytokinin-like plant growth regulator, which could be used in promoting shoot proliferation.

TABLE 22

Transformation frequency and quality observed from whole regenerated explants.

| Protocol & vector type | # Explants | # Events produced | TF % | # Events assayed | % quality events | qTF % | Estimated mTF %** |
|---|---|---|---|---|---|---|---|
| Dry Excised-2T/OriV | 260 | 34 | 13.1 +/− 0.17 | 32 | 21.9 | 2.7 +/− 0.23 | 0.62 |
| Dry Excised-2T/OriRi | 161 | 15 | 9.32 +/− 7.38 | 14 | 28.6 | 2.5 | 0.45 |
| Pre-cultured Dry-2T/OriV | 1641 | 319 | 19.4 +/− 5.42 | 311 | 24.4 | 4.6 +/− 1.35 | 1.1 |
| Pre-cultured Dry-2T/OriRi | 336 | 66 | 19.64 +/− 1.97 | 64 | 20.3 | 3.9 +/− 1.22 | 0.7 |

Example 16

Production of Transgenic Soybean Plants Using Stored Dry Soybean Embryos, Spectinomycin, and Transfer of Whole Regenerated Explant with a Pre-Culturing Step In this example, 3 months stored dry explants were used, and a 1 hr hydration step carried out in INO was utilized, on dry excised explants. Pre-culturing was performed for 5 days at 23° C. in dark conditions in BGM with 50 ppm nystatin and 10 ppm TBZ (thiabendazole) fungicides (nystatin and TZB Stock is made as by dissolving 50,000 ppm Nystatin and 10,000 ppm TBZ in pure DMSO, diluted 1000 fold (1 ml of stock in 1L of INO)). TDZ (1.0 ppm) and lipoic acid were both added to the inoculum and to the co-culture media (INO). The construct, pMON107379, was a conventional 2T vector comprising oriRi and aadA gene, and co-culture was done for 5 days. After co-culture the explants were surface plated on solid WPM and then transferred to the Oasis® Wedge System (Smithers-Oasis USA; Kent, Ohio) with a simplified liquid medium (0.5 g/L WPM with 0.25 mg/L IBA). As shown in Table 23, pre-culturing dry explants boosted TF. Thus, 3 month old stored dry explants could perform similarly to freshly excised dry explants. The addition to INO Co-culture media of nystatin (50 ppm) and thiabendazole (10 ppm) dissolved in DMSO (1.0 ml of DMSO per liter of INO) improved the health of explants, likely by controlling yeasts and fungi commonly found in and on seeds and therefore can be beneficial when performing large and/or automated tissue culture.

TABLE 23

Effect of pre-culture on TF (%) of stored dry explants.

| Explant type | Pre-culture step | # Explants | R0 plants | TF |
|---|---|---|---|---|
| Wet Excised | No | 263 | 75 | 28.52% |
| Stored Dry Explants | No | 678 | 71 | 10.47% |
| Fresh Dry Explants | No | 375 | 24 | 6.40% |
| Stored Dry Explants | Yes | 901 | 129 | 14.32% |
| Fresh Dry Explants | Yes | 1008 | 112 | 11.11% |

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

REFERENCES

The following references, to the extent that they provide exemplary procedural or other details supplementary to those set forth herein, are specifically incorporated herein by reference.

U.S. Pat. No. 5,217,902
U.S. Pat. No. 5,914,451
U.S. Pat. No. 6,384,301
U.S. Pat. No. 7,002,058
U.S. Pub. 20050005321
U.S. Pub. 20060059589
U.S. Pub. 20070271627
U.S. Pub. 20070074314
Broothaerts et al., *Nature*, 433:629-633, 2005.
Chai et al., *Seed Science Research* 8 (Supplement 1):23-28, 1998.
Chu et al., *Sci. Sinica* 18:659-668, 1975.
Duncan et al., *Planta* 165:322-332, 1985.
Gamborg et al., *Exp Cell Res.* 50:151-8, 1968.
Linsmaier and Skoog, *Physiol. Plant.* 18: 100-127, 1965.
McCabe et al., *Bio/Technology* 6:923-926, 1988.
McCabe and Martinell, *Bio/Technology* 11:596-598, 1993.
Mein et al., *Genome Res.* 10:330-343, 2001.
Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, pages 67-88, 1993.
Miki and McHugh, *J. Biotechnol.*, 107: 193-232, 2004.
Murashige and Skoog, *Physiol. Plant.* 15: 473-497, 1962.
McCown and Lloyd, Combined Proc.—Int. Plant Propagator's Soc., 30: 421-427, 1981.
Nitsch and Nitsch, *Science* 163:85-87 1969.
Sandvang, *Antimicrob. Agents Chemotherapy* 43:3036-3038, 1999.
Schenk and Hildebrandt, *Can. J. Bot.* 50:199-204, 1972.
Senaratna et al., *Pl. Physiol.* 72:620-624, 1983.
Uchimiya and Murashige, *Plant Physiol.* 57: 424-429, 1976.
Vertucci and Roos, *Pl. Physiol.* 90:1019-1023, 1990.
Zambre et al., *Planta* 216:580-586, 2003.

What is claimed is:

1. A method for preparing transformable and regenerable explant material comprising meristematic tissue from a singulated plant seed, comprising:
   a) subjecting the singulated seed that comprises a seed coat, a cotyledon tissue, and a meristematic tissue to a force sufficient to fracture the seed; and
   b) separating an explant comprising the meristematic tissue from the seed coat and optionally the cotyledon tissue, wherein the method is mechanized;
   wherein the seed from which the explant is separated comprises an internal moisture content of from about 4% to about 16%; and wherein the subjecting and separating is performed in the absence of a liquid.

2. The method of claim 1, further comprising the step of:
   (c) transforming at least a first cell of the explant with a selected DNA.

3. The method of claim 2, further comprising the step of:
   (d) regenerating a transgenic plant from said cell, wherein the plant is stably transformed with the selected DNA.

4. The method of claim 3, further defined as comprising storing the explant prior to step (d) under conditions wherein the explant does not germinate.

5. The method of claim 4, wherein the explant material is stored for from about 1 hour to about 20 months.

6. The method of claim 4, wherein the explant is stored at a temperature of between about −80° C. and about 60° C.

7. The method of claim 4, wherein the explant is dehydrated prior to storing.

8. The method of claim 1, wherein the explant comprises an internal moisture content of from about 3% to about 25%.

9. The method of claim 1, wherein the explant has an internal moisture content of from about 4% to about 11%.

10. The method of claim 1, further defined as comprising preparing a plurality of explants from a plurality of seeds and selecting one or more explant exhibiting at least a first characteristic indicative of the ability to transform the explant and/or regenerate a plant from the explant.

11. The method of claim 10, wherein the characteristic is selected from the group consisting of color, size, shape, density, proximate analysis, carbohydrate content, protein content, fat content, fibre (ash) content, moisture content, viability, germplasm, intactness, pathogen presence, and optical characteristics.

12. The method of claim 1, wherein the plant seed is a soybean, canola, corn, cotton, onion, pepper, tomato, cucurbit, rice, or wheat seed.

13. A method for preparing transformable and regenerable explant material comprising meristematic tissue from a singulated plant seed, comprising:
   a) subjecting the singulated seed that comprises a seed coat, a cotyledon tissue , and a meristematic tissue to a force sufficient to fracture the seed;
   b) separating an explant comprising the meristematic tissue from the seed coat and optionally the cotyledon tissue, wherein the method is mechanized; and
   c) storing the explant for from about 1 hour to about 20 months under conditions wherein the explant does not germinate and remains viable and competent for germination or genetic transformation;
   wherein the seed from which the explant is separated comprises an internal moisture content of from about 4% to about 16%; and wherein the subjecting and separating is performed in the absence of a liquid.

14. The method of claim 13, further comprising the step of transforming at least a first cell of the explant with a selected DNA.

15. The method of claim 13, wherein the explant is stored at a temperature of between about −80° C. and about 60° C.

16. The method of claim 13, wherein the explant is dehydrated prior to storing.

17. The method of claim 13, wherein the explant has an internal moisture content of from about 4% to about 11%.

18. The method of claim 13, wherein the plant seed is a soybean, canola, corn, cotton, onion, pepper, tomato, cucurbit, rice, or wheat seed.

19. The method of claim 1, wherein the plant seed is a soybean, canola, corn, cotton, onion, pepper, tomato, cucurbit, rice, or wheat seed.

20. The method of claim 13, further comprising the step of:
   (c) transforming at least a first cell of the explant with a selected DNA.

21. The method of claim 14, further comprising the step of:
   (d) regenerating a transgenic plant from said cell, wherein the plant is stably transformed with the selected DNA.

* * * * *